US010337052B2

(12) United States Patent
Kim et al.

(10) Patent No.: US 10,337,052 B2
(45) Date of Patent: Jul. 2, 2019

(54) METHOD FOR TESTING A MUTANT GENE THROUGH REAL TIME POLYMERASE CHAIN REACTION USING INHIBITION OF 5'-FLAP ENDONUCLEASE ACTIVITY

(71) Applicant: GENOTECH CORP., Daejeon (KR)

(72) Inventors: Jae Jong Kim, Daejeon (KR); Sun Ho Cha, Daejeon (KR); Si Kyu Lim, Daejeon (KR)

(73) Assignee: GENOTECH CORP., Daejeon (KR)

(*) Notice: Subject to any disclaimer, the term of this patent is extended or adjusted under 35 U.S.C. 154(b) by 55 days.

(21) Appl. No.: 15/110,713

(22) PCT Filed: Jan. 8, 2015

(86) PCT No.: PCT/KR2015/000167
§ 371 (c)(1),
(2) Date: Jul. 8, 2016

(87) PCT Pub. No.: WO2015/105336
PCT Pub. Date: Jul. 16, 2015

(65) Prior Publication Data
US 2016/0326577 A1 Nov. 10, 2016

(30) Foreign Application Priority Data

Jan. 8, 2014 (KR) ........................ 10-2014-0002306

(51) Int. Cl.
C12Q 1/68 (2018.01)
C12Q 1/6827 (2018.01)
C12Q 1/686 (2018.01)

(52) U.S. Cl.
CPC ........... *C12Q 1/6827* (2013.01); *C12Q 1/686* (2013.01)

(58) Field of Classification Search
CPC .................. C12Q 1/686; C12Q 1/6827; C12Q 2521/307; C12Q 2535/131; C12Q 2561/113
See application file for complete search history.

(56) References Cited

U.S. PATENT DOCUMENTS

2008/0118922 A1 5/2008 Matsui et al.

FOREIGN PATENT DOCUMENTS

| KR | 10-2010-0129767 A | 12/2010 |
| KR | 10-2011-0093323 A | 8/2011 |
| KR | 10-2012-0046018 A | 5/2012 |
| KR | 10-2013-0091939 A | 8/2013 |

OTHER PUBLICATIONS

Leclerc et al. *Homo sapiens* 5-methyltetrahydrofolate-homocysteine methyltransferase reductase (MTRR), RefSeqGene on chromosome 5. NCBI Reference Sequence: NG_008856.1 (1999), pp. 1-13.*
Lee et al., "Homogeneous Fluorescent Chemistries for Real-Time PCR", Real-Time PCR: Current Technology and Jan. 2009, Chapter 3—40 pages.
Punia et al.,"The Quantitative Amplification Refractory Mutation System", Real time PCR : an essential guide, Horizon Bioscience, May 2004, Chapter 6—17 pages.
Lieber, "The FEN-1 family of structure-specific nucleases in eukaryotic DNA replication, recombination and repair", 1997, BioEssays, vol. 19, No. 3, pp. 233-240.
International Search Report dated Apr. 20, 2015 of PCT/KR2015/000167 which is the parent application and its English translation—6 pages.
Olivier, M., "The Invader assay for SNP genotyping", Mutation Research, Jun. 3, 2005, vol. 573(1-2), pp. 1-9.
Hsu et al., "Genotyping Single-Nucleotide Polymorphisms by the Invader Assay with Dual-Color Fluorescence Polarization Detection", Clinical Chemistry, Aug. 2001, vol. 47, No. 8, pp. 1373-1377.
Birdsell et al., "Melt Analysis of Mismatch Amplification Mutation Assays (Melt-MAMA): A Functional Study of Cost-Effective SNP Genotyping Assay in Bacterial Models", PLoS One, Mar. 16, 2012, vol. 7, No. 3, pp. 1-18.
Li et al., "Genotyping with TaqMAMA", Genomics, 2004, vol. 83, No. 2, pp. 311-320.
Tsutakawa et al., "Human Flap Endonuclease Structures, DNA Double-Base Flipping, and a Unified Understanding the of FEN1 Superfamily", Cell, Apr. 15, 2011, vol. 145, No. 2, pp. 198-211.
Tomlinson et al., "Substrate Recognition and Catalysis by Flap Endonucleases and Related Enzymes", Biochem. Soc. Trans., Apr. 2010, vol. 38, No. 2, pp. 433-437.
Liu et al., "Functional FEN1 genetic variants contribute to risk of hepatocellular carcinoma, esophageal cancer, gastric cancer and colorectal cancer", Carcinogenesis, 2012, vol. 33, No. 1, pp. 119-123.
Lyamichev et al., "Comparison of the 5* nuclease activities of Taq DNA polymerase and its isolated nuclease domain", Proc. Natl. Acad. Sci., May 1999, vol. 96, pp. 6143-6148.
Ulvik et al., "Single Nucleotide Polymorphism (SNP) Genotyping in Unprocessed Whole Blood and Serum by Real-Time PCR: Application to SNPs Affecting Homocysteine and Folate Metabolism", Clinical Chemistry, 2001, vol. 47, No. 11, pp. 2050-2053.
Wittwer et al., "Continuous Fluorescence Monitoring of Rapid Cycle DNA Amplification", BioTechniques, Jan. 1997, vol. 22, pp. 130-138.

(Continued)

Primary Examiner — David C Thomas
(74) Attorney, Agent, or Firm — Knobbe Martens Olson & Bear LLP

(57) ABSTRACT

The present invention relates to a method for detecting single nucleotide polymorphism (SNP) using a feature that the 5'-flap endonuclease (FEN) activity of DNA polymerase is inhibited when a probe complementarily binds to the end of a polymerase chain reaction (PCR) product. More specifically, the present invention relates to a novel method wherein it was verified that, when a probe used for a real-time PCR complementarily binds to the end site of a PCR product, the 5'-FEN activity of thermostable DNA polymerase to the probe is inhibited, and thus when such a feature is used to make a design such that an SNP site to be detected is located at the 5'-end site of the probe, the 5'-flap formation is induced according to the allele, thereby allowing effective SNP detection.

8 Claims, 27 Drawing Sheets

Specification includes a Sequence Listing.

(56) References Cited

OTHER PUBLICATIONS

Lohmann et al., "Fast and Flexible Single Nucleotide Polymorphism (SNP) Detection with the LightCycler System", Biochemica, 2000, No. 4, pp. 23-28.

Harrington et al., "The characterization of a mammalian DNA structure-specific endonuclease", The EMBO Journal, 1994, vol. 13, No. 5, pp. 1235-1246.

Letertre et al., "Evaluation of the performance of LNA and MGB probes in 50'-nuclease PCR assays", Molecular and Cellular Probes, 2003, vol. 17, pp. 307-311.

Kutyavin et al., "3'-Minor groove binder-DNA probes increase sequence specificity at PCR extension temperatures", Nucleic Acids Research, 2000, vol. 28, No. 2, pp. 655-661.

Ellison et al., "A comparison of ARMS and DNA sequencing for mutation analysis in clinical biopsy samples", Journal of Experimental & Clinical Cancer Research, 2010, vol. 29, No. 132, pp. 1-8.

Bonnet et al., "Thermodynamic basis of the enhanced specificity of structured DNA probes", Proc. Natl. Acad. Sci. USA, May 1999, vol. 96, pp. 6171-6176.

Broude, "Stem-loop oligonucleotides: a robust tool for molecular biology and biotechnology", Trends in Biotechnology, Jun. 2002, vol. 20, No. 6, pp. 249-256.

Tapp et al., "Homogeneous Scoring of Single-Nucleotide Polymorphisms: Comparison of the 5'-Nuclease TaqMan Assay and Molecular Beacon Probes", BioTechniques, Apr. 2000, vol. 28, pp. 732-738.

Holland et al., "Detection of specific polymerase chain reaction product by utilizing the 5'-3' exonuclease activity of Thermus aquaticus DNA polymerase", Proc. Natl. Acad. Sci. USA, Aug. 1991, vol. 88, pp. 7276-7280.

Heid et al., "Real Time Quantitative PCR", Genome Research, 1996, vol. 6, pp. 986-994.

Rossi et al., "Lagging Strand Replication Proteins in Genome Stability and DNA Repair", Chem. Rev., 2006, vol. 106, pp. 453-473.

Kim et al., "Involvement of Flap Endonuclease 1 in Base Excision DNA Repair", The Journal of Biological Chemistry, 1998, vol. 273, No. 15, pp. 8842-8848.

Klungland et al., "Second pathway for completion of human DNA base excision-repair: reconstitution with purified proteins and requirement for DNase IV (FEN1)", 1997, The EMBO Journal, vol. 16, No. 11, pp. 3341-3348.

McWhirter et al., "Development of a High-Throughput Fluorescence Polarization DNA Cleavage Assay for the Identification of FEN1 Inhibitors", 2013, Journal of Biomolecular Screening, vol. 18, No. 5, pp. 567-575.

Lyamichev et al., "Structure-Specific Endonucleolytic Cleavage of Nucleic Acids by Eubacterial DNA Polymerases", Science, May 7, 1993, vol. 260, pp. 778-783.

Livak et al., "Allelic discrimination using fluorogenic probes and the 5' nuclease assay", Genetic Analysis: Thomolecular Engineering, 1999, vol. 14, pp. 143-149.

Li et al., "A new class of homogeneous nucleic acid probes based on specific displacement hybridization", Nucleic Acids Research, 2002, vol. 30, No. 2e5, pp. 1-9.

TaqMan® SNP Genotyping Assays Protocol, Part No. 4332856 Rev. D, Applied Biosystems, pp. 1-60.

Sachidanandam et al., "A map of human genome sequence variation containing 1.42 million single nucleotide polymorphisms", Nature, Feb. 15, 2001, vol. 409, pp. 928-933.

Li et al., "Low Nucleotide Diversity in Man", Genetics, Oct. 1991, vol. 129, pp. 513-523.

Kim et al., "SNP Genotyping: Technologies and Biomedical Applications", 2007, Annu. Rev. Biomed. Eng., vol. 9, pp. 289-320.

Syvanen, "Accessing Genetic Variation: Genotyping Single Nucleotide Polymorphisms", Nat. Rev. Genet., Dec. 2001, vol. 2, pp. 930-942.

Kirk et al., "Single nucleotide polymorphism seeking long term association with complex disease", Nucleic Acids Research, 2002, vol. 30, No. 15, pp. 3295-3311.

Kwok, "SNP Genotyping With Fluorescence Polarization Detection", Human Mutation, 2002, vol. 19, pp. 315-323.

\* cited by examiner

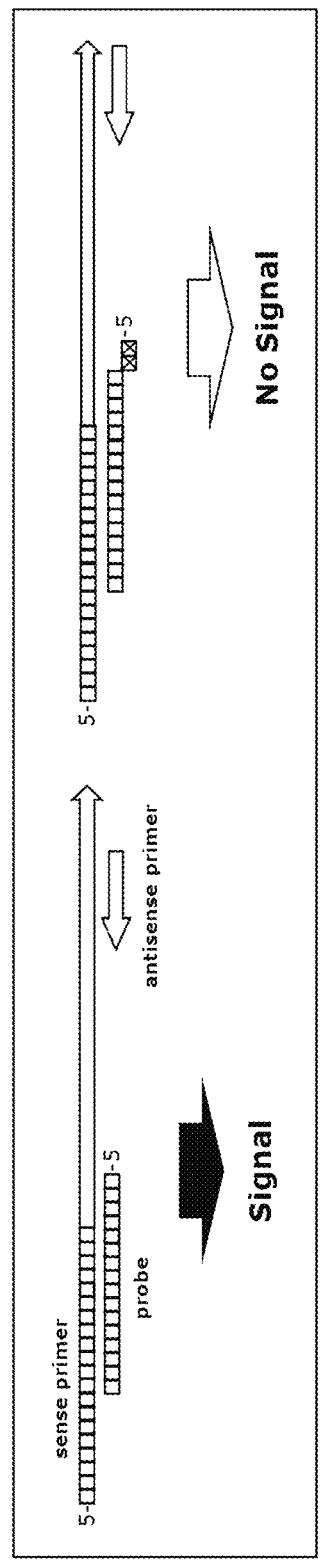
[Fig. 1a]

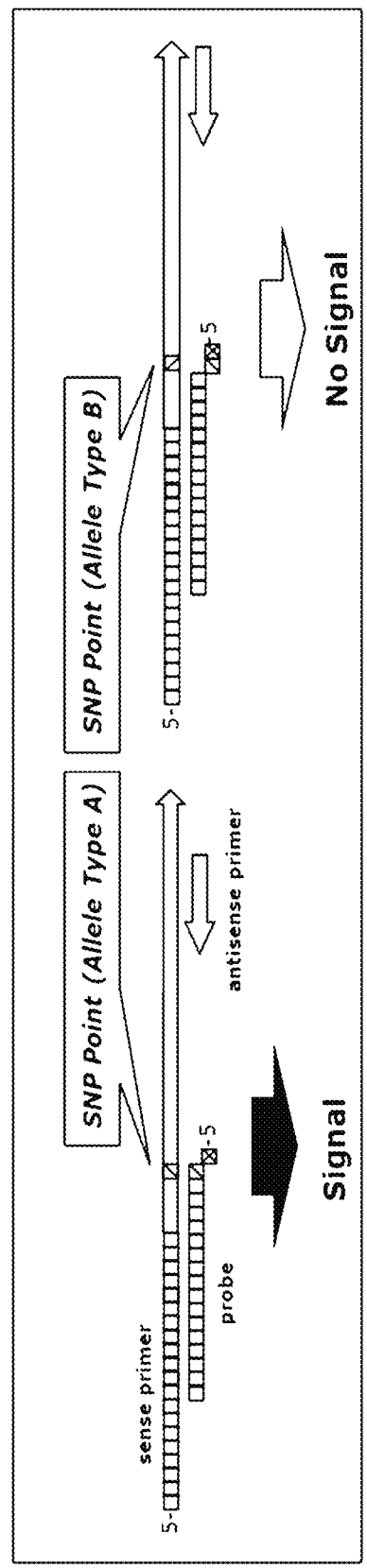
[Fig. 1b]

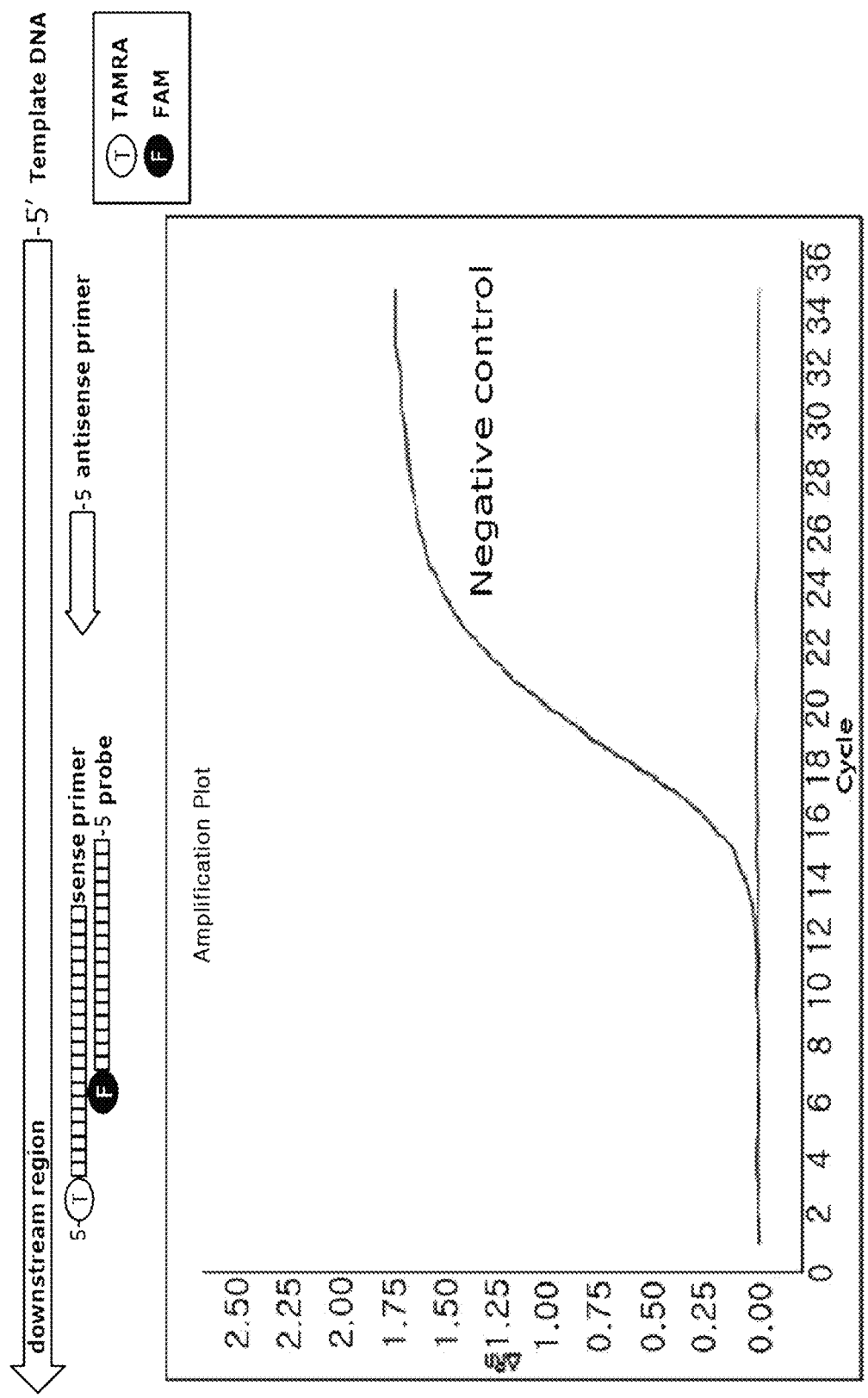

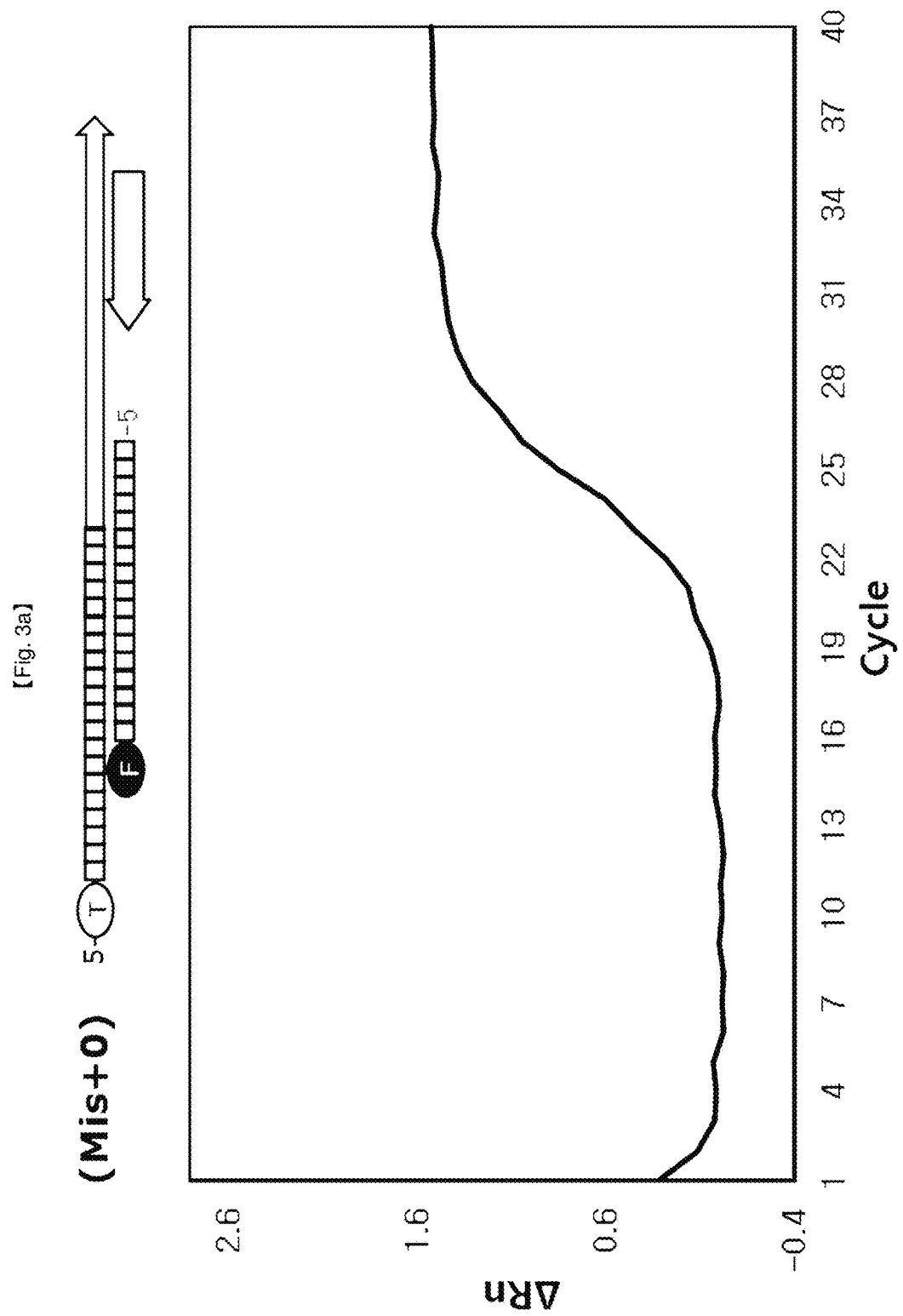

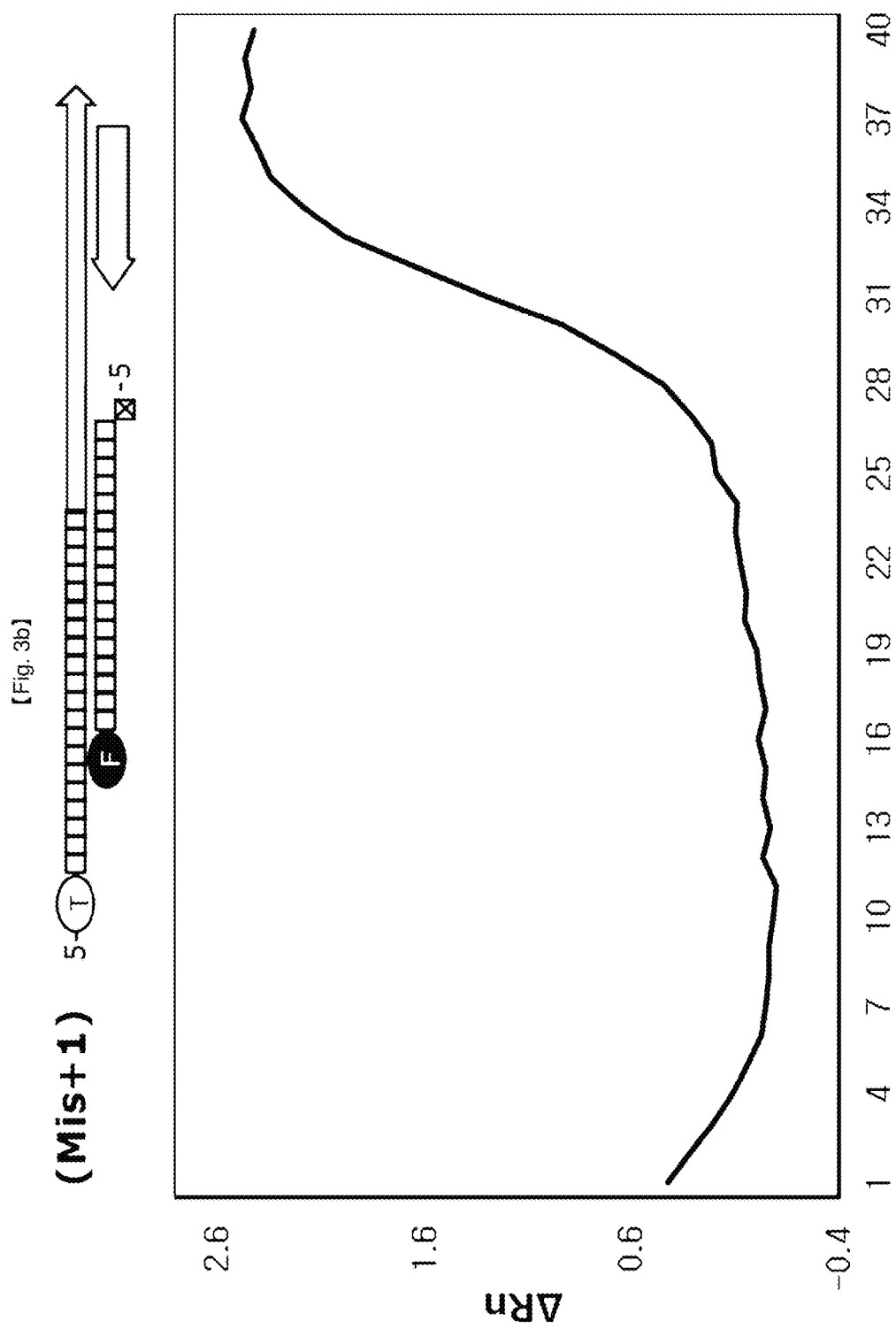

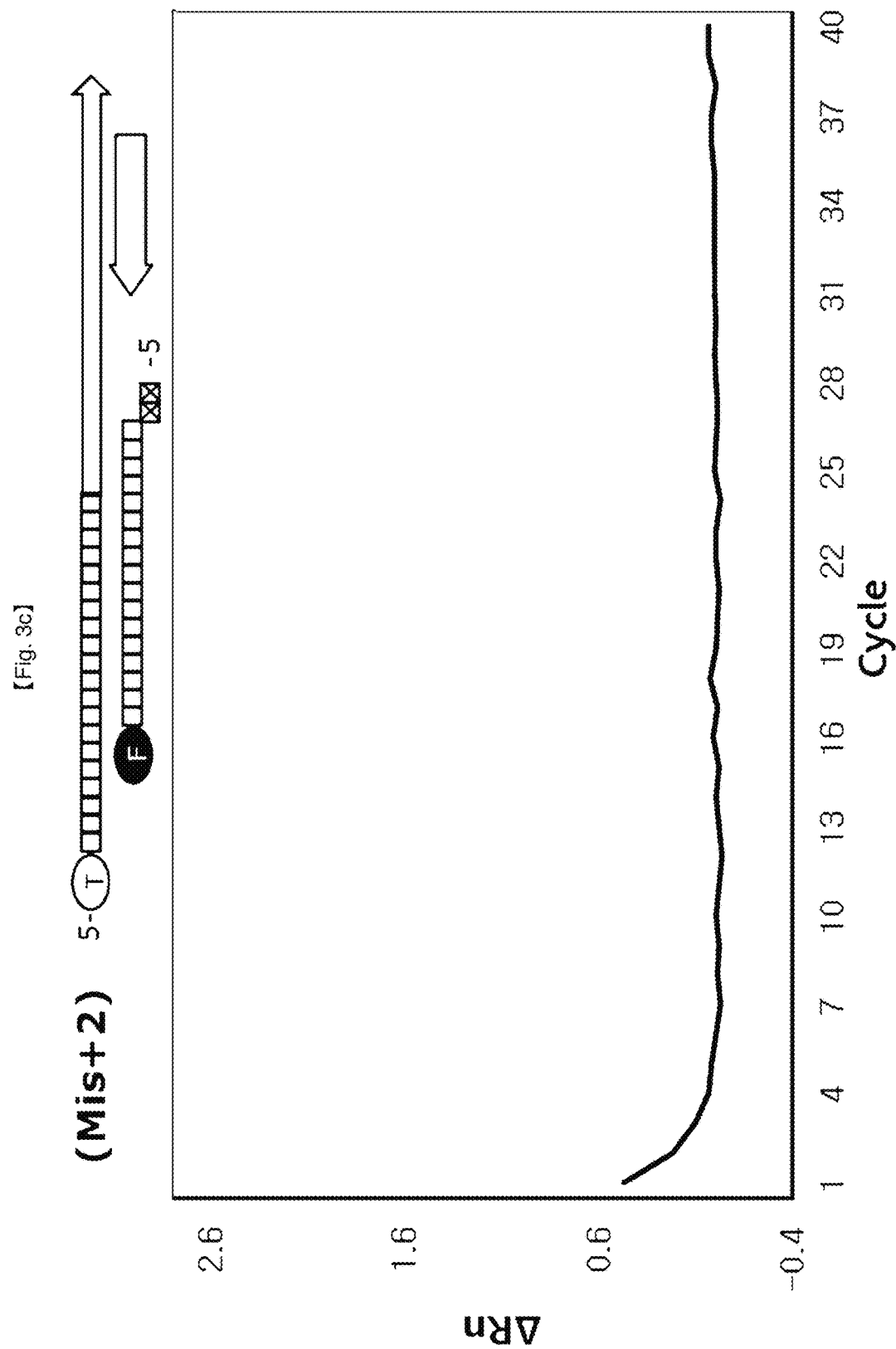

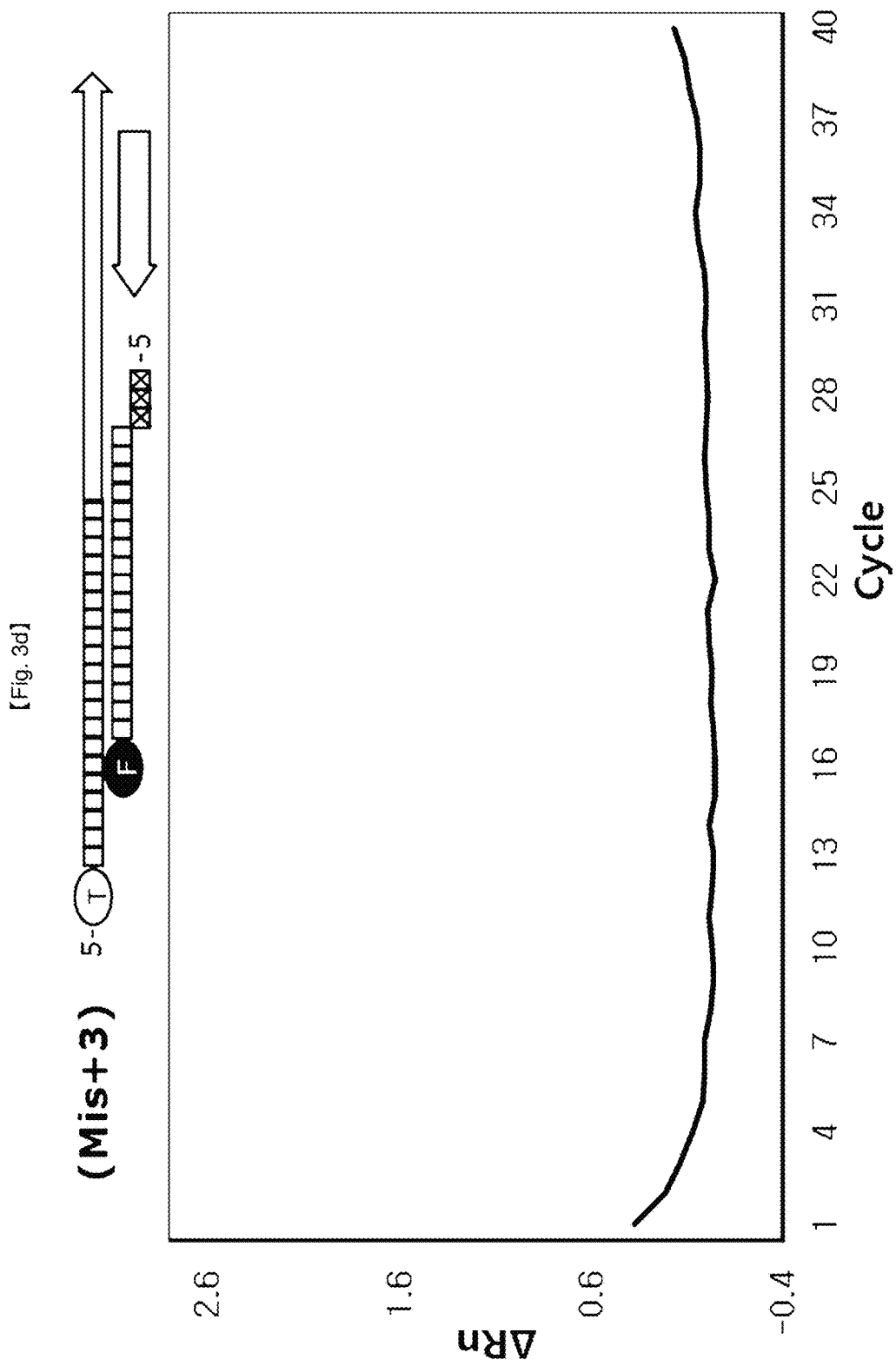

[Fig. 4a]
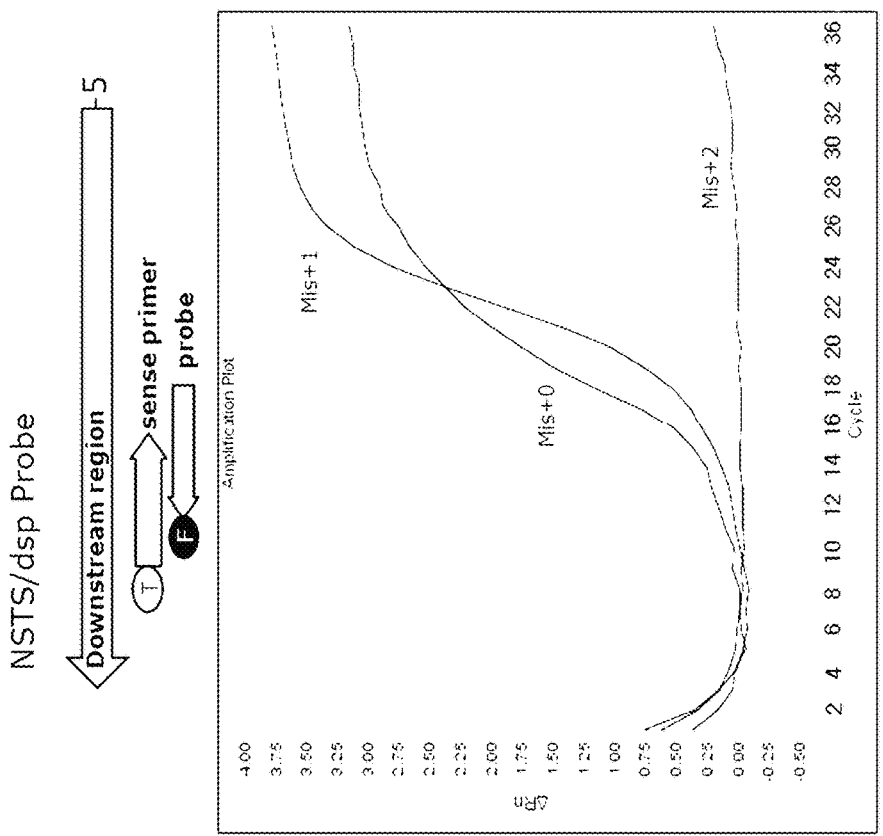

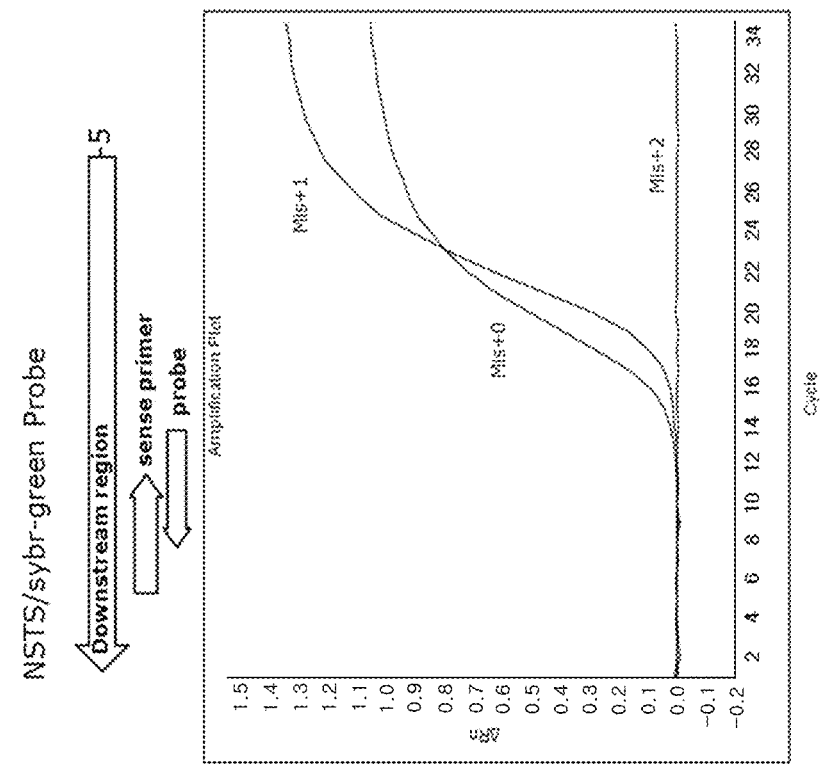
[Fig. 4b]
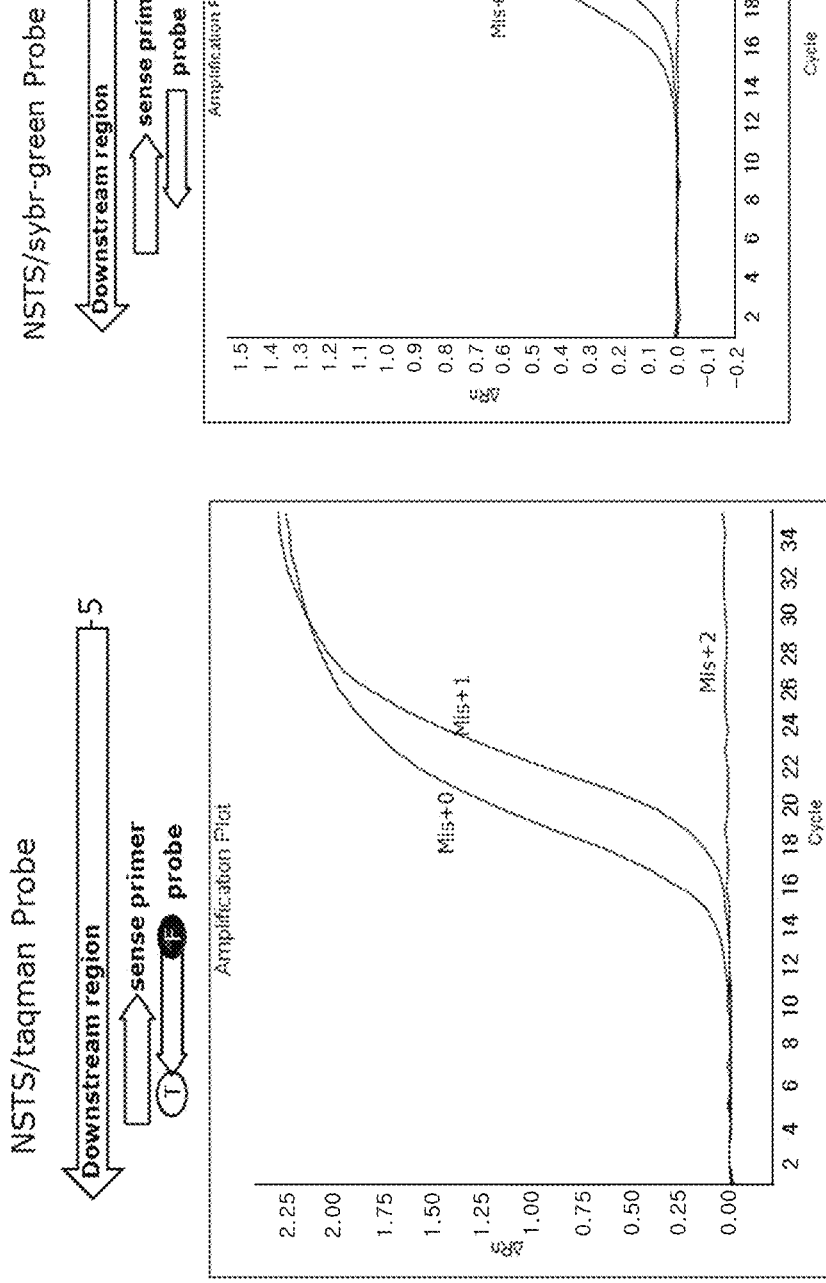
[Fig. 5a]

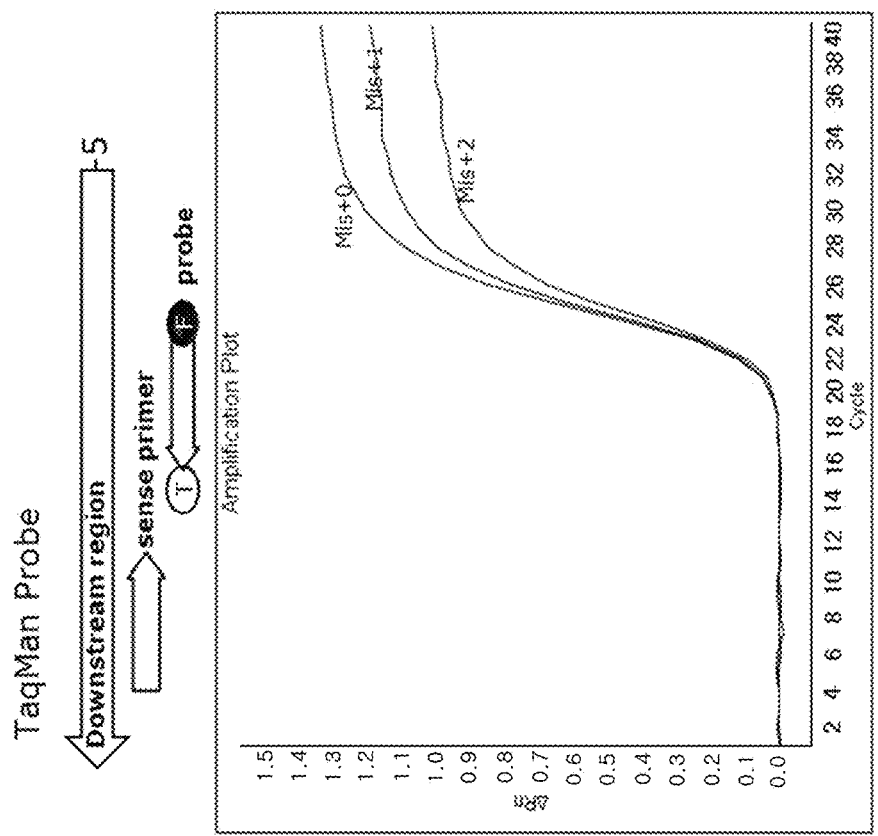
[Fig. 5b]

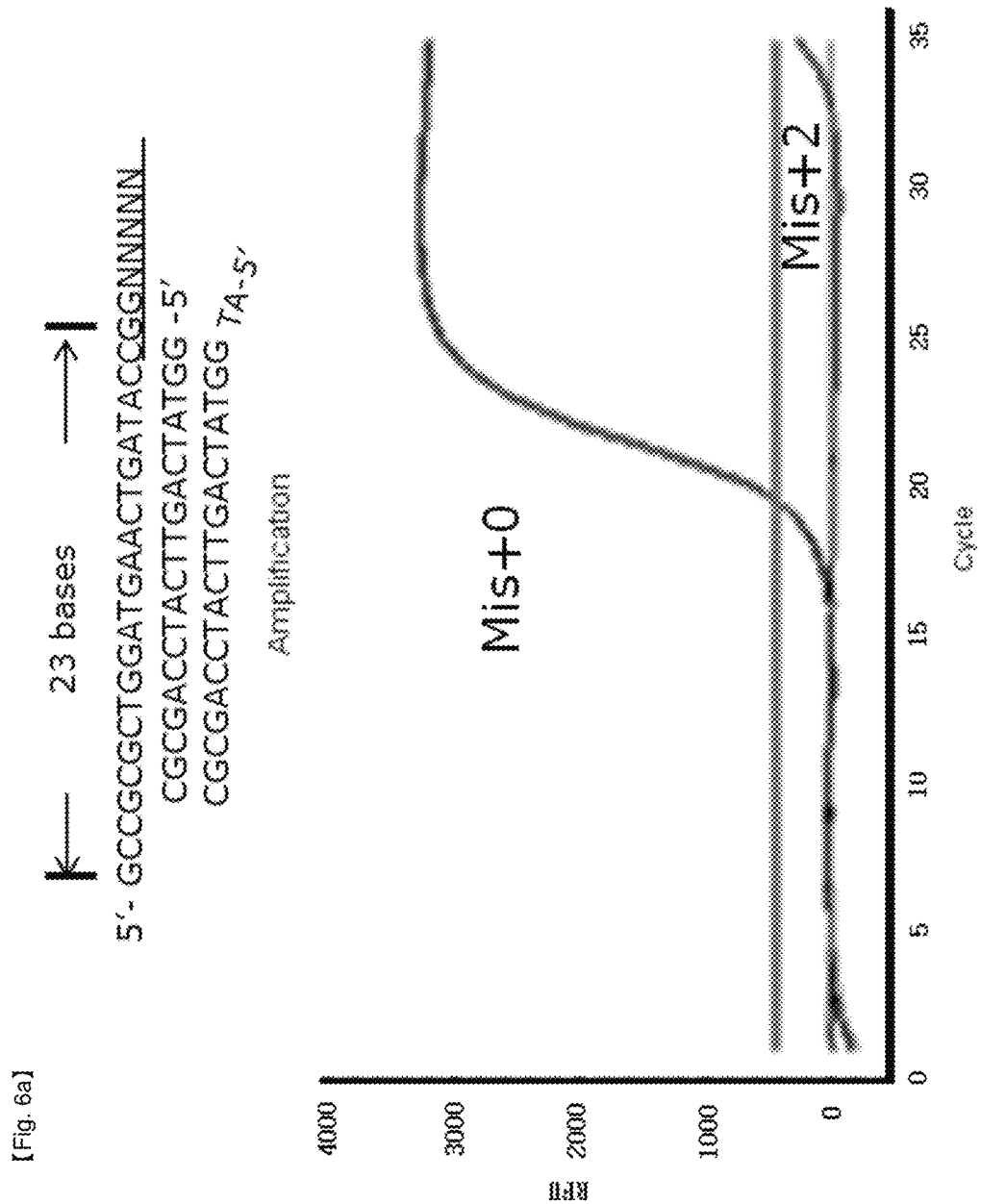

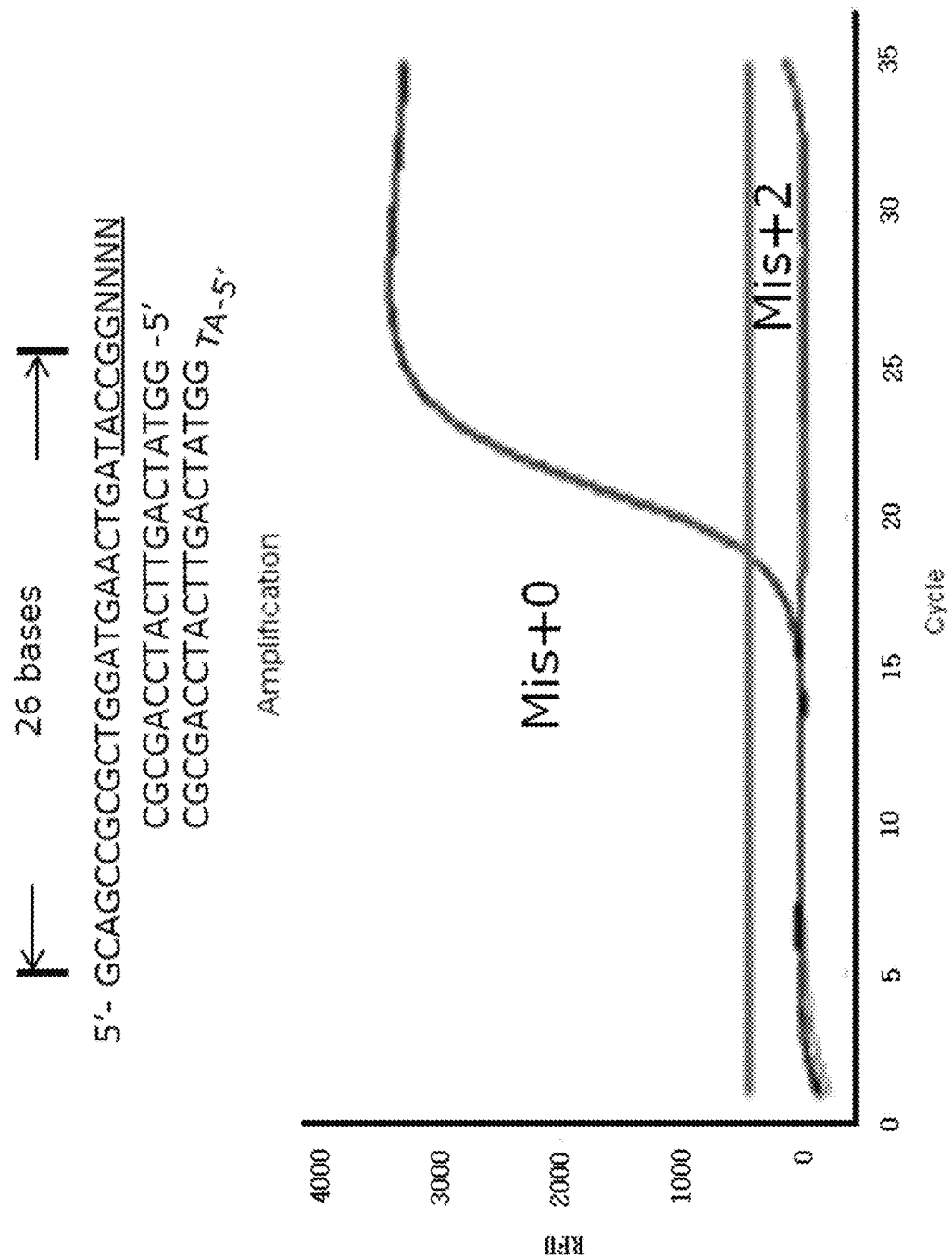

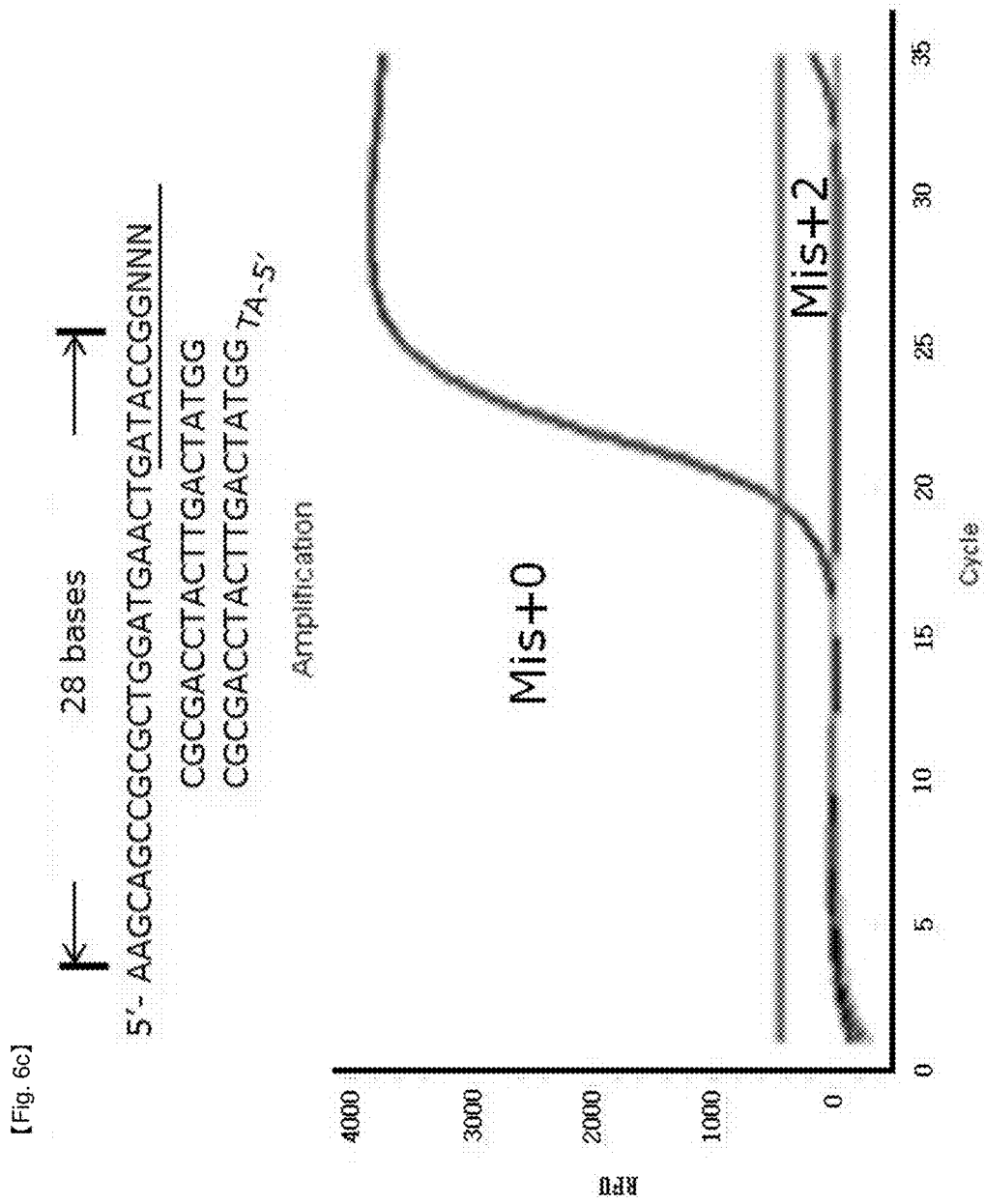

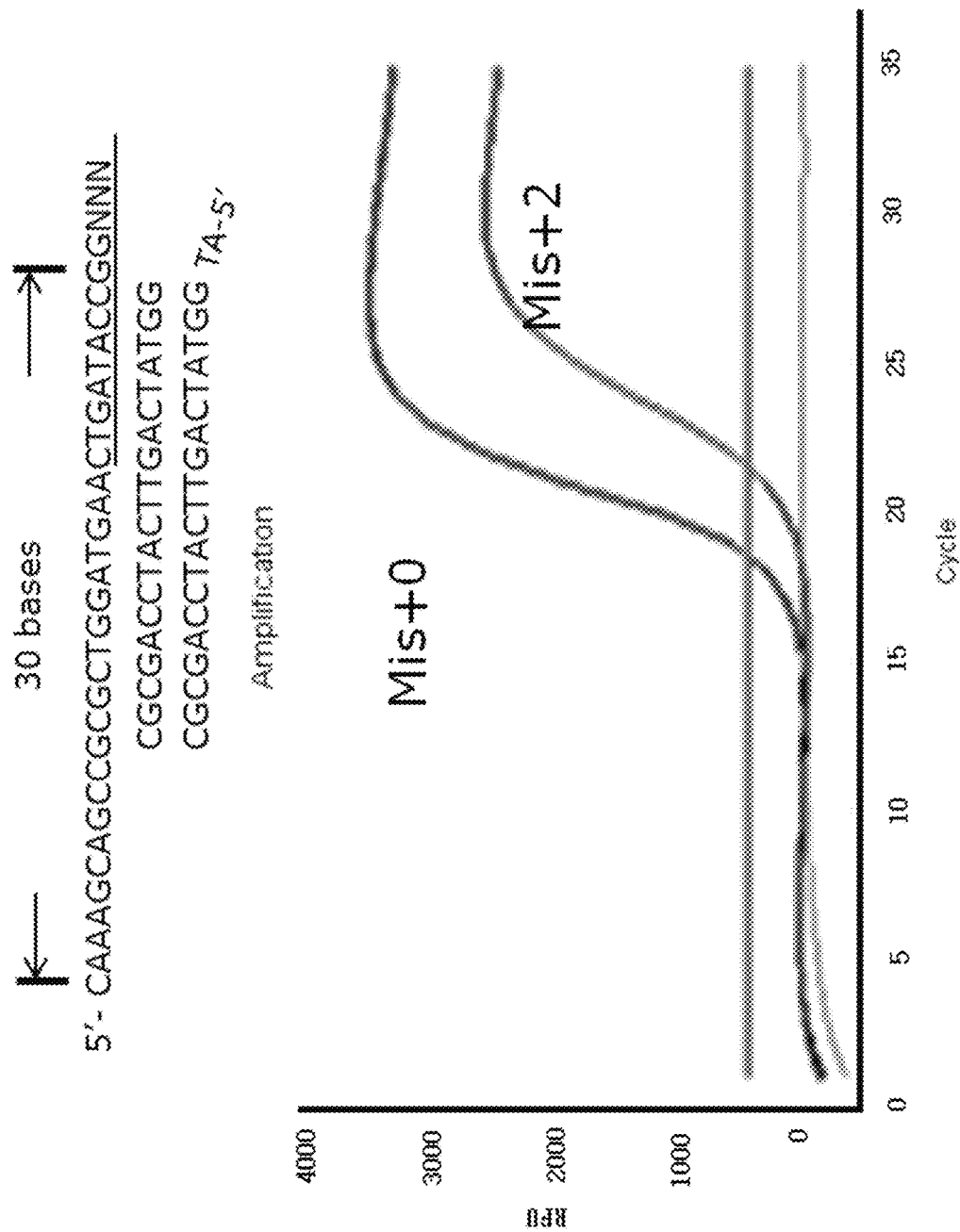
[Fig. 6d]

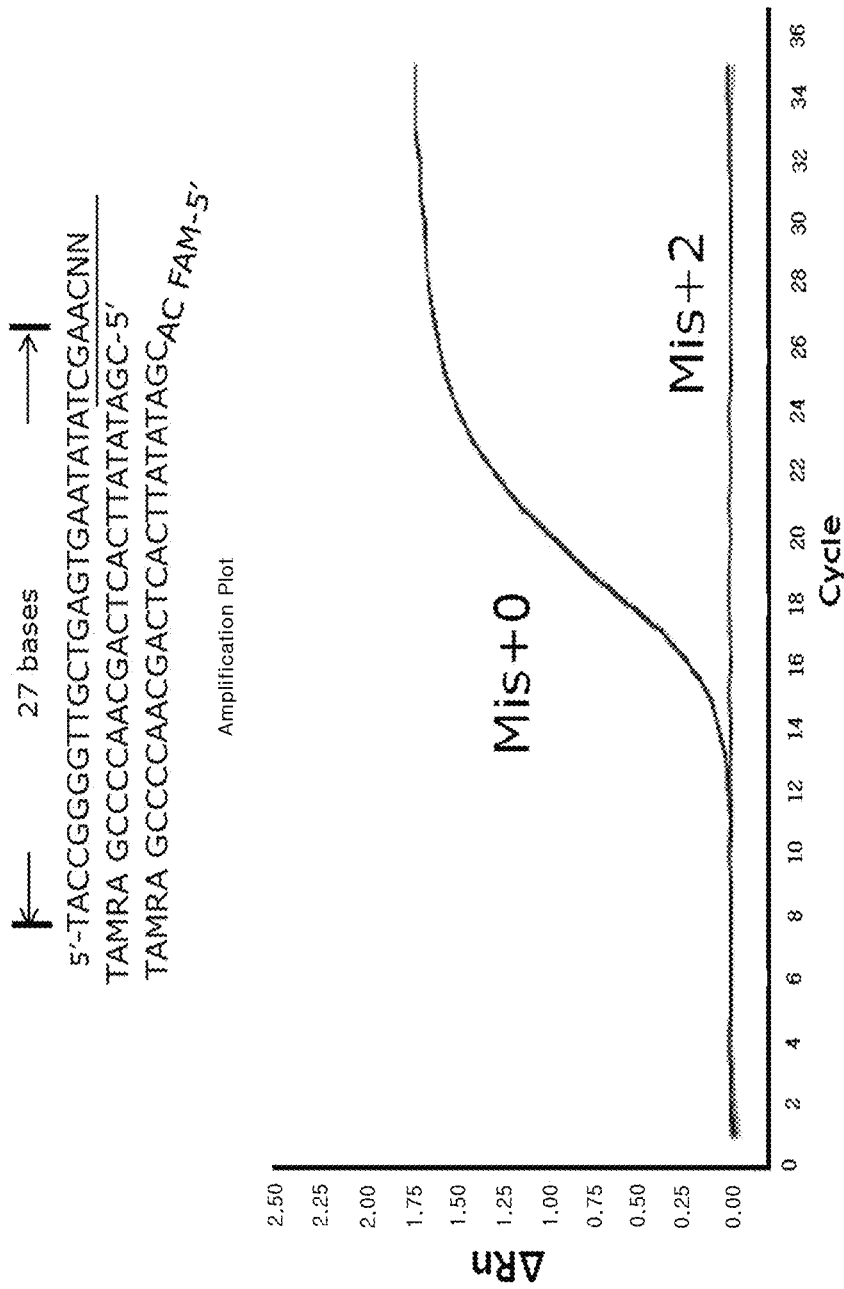
[Fig. 7a]

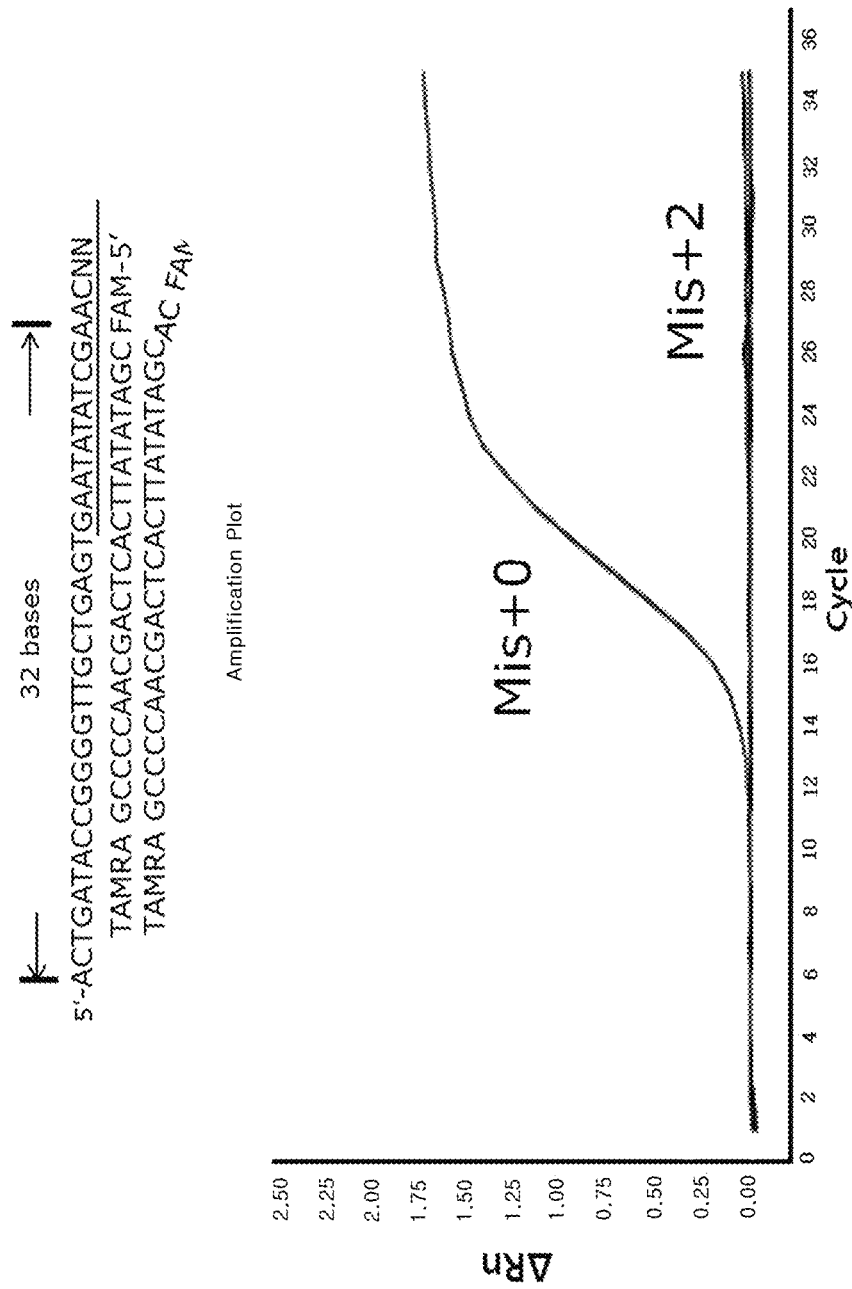

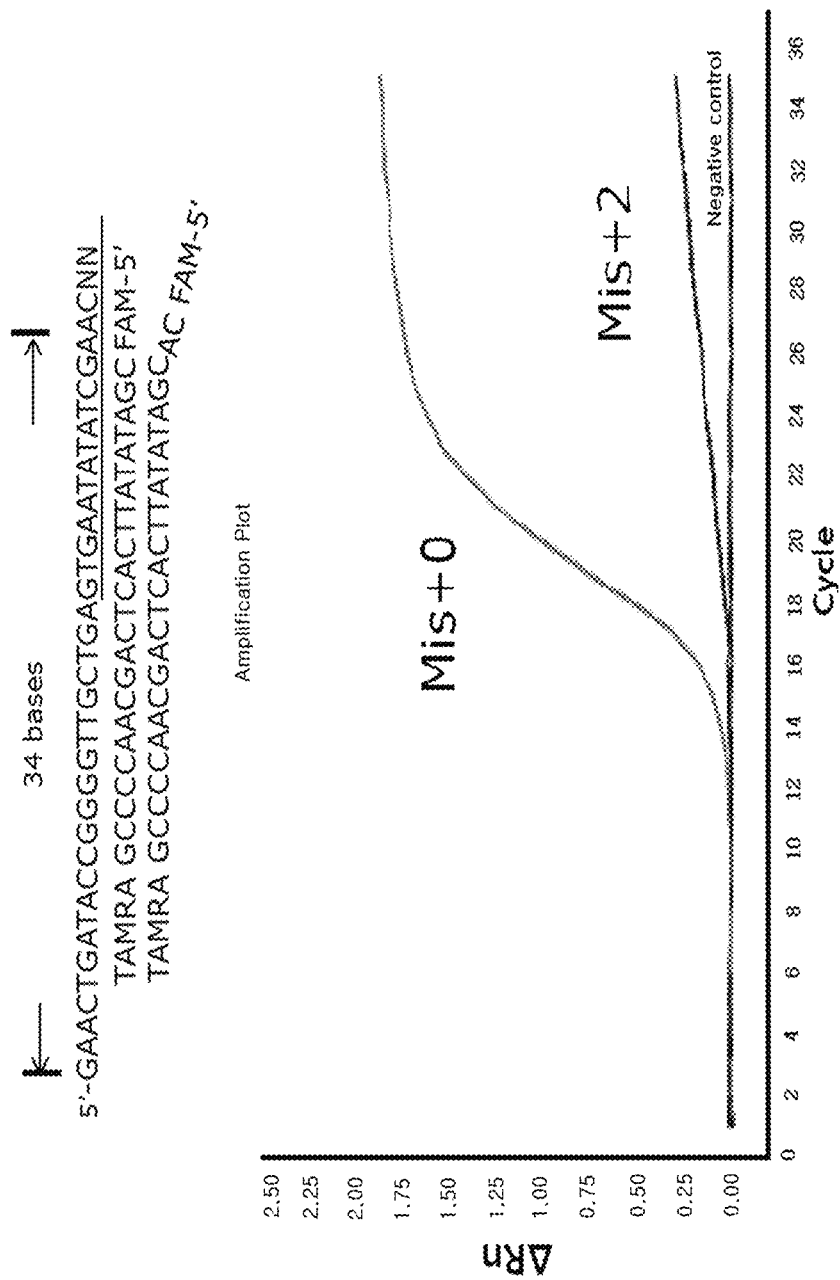
[Fig. 7c]

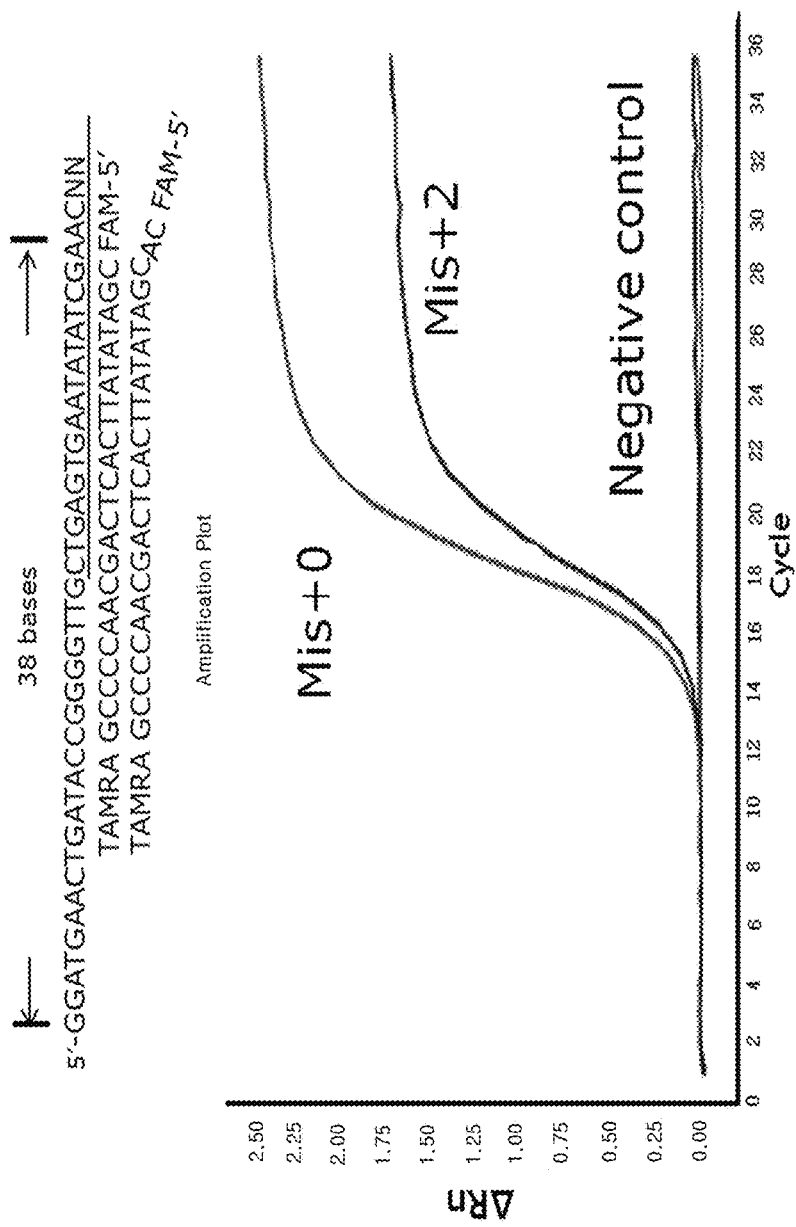
[Fig. 7d]

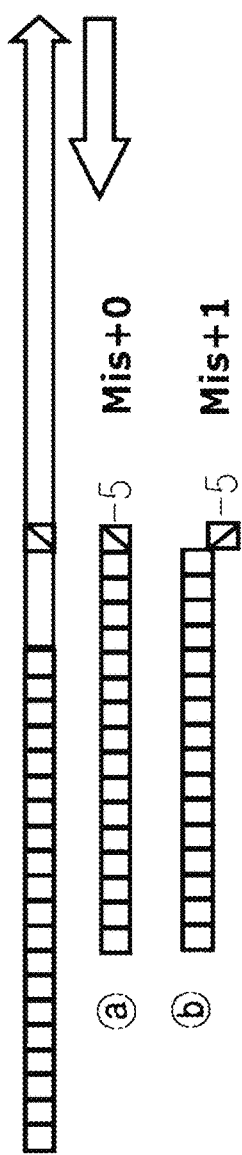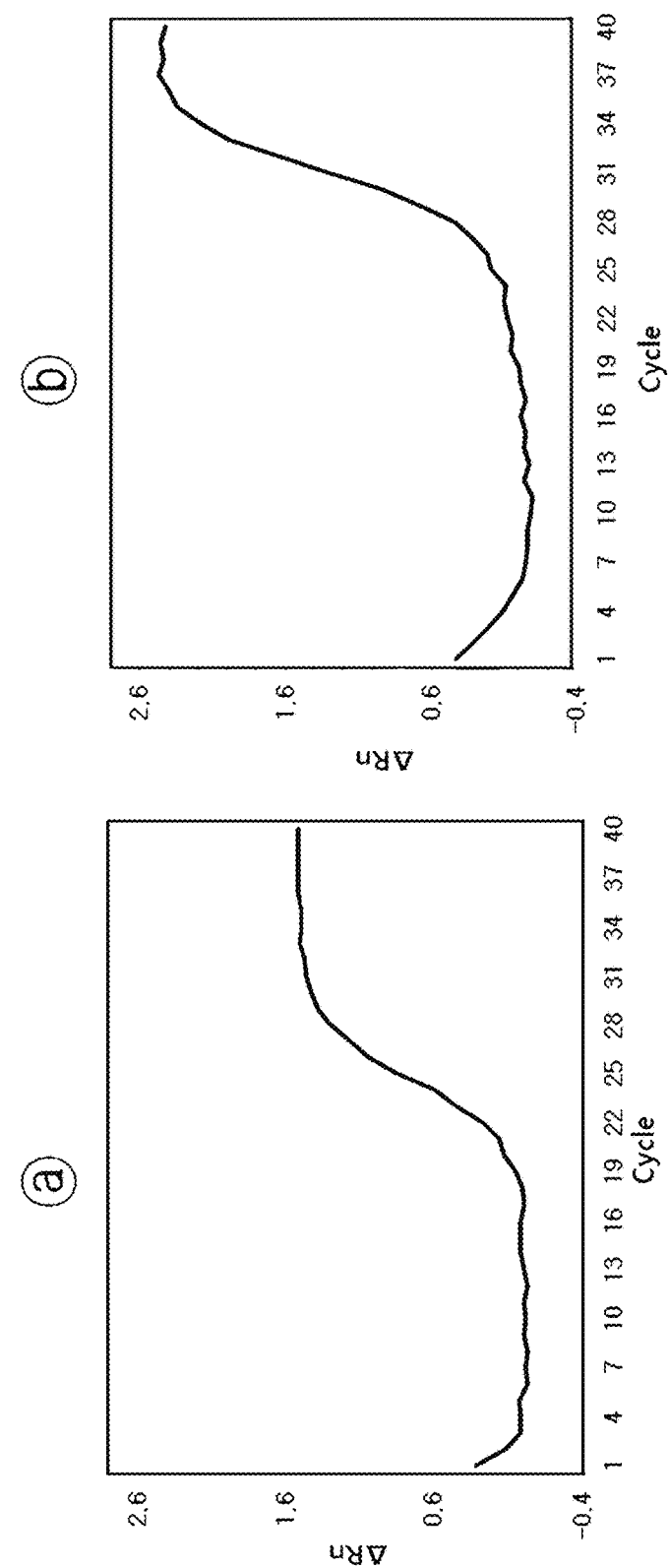
[Fig. 8a]

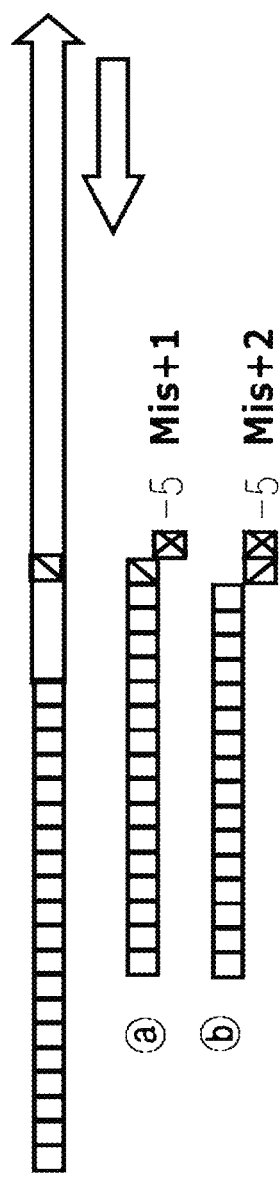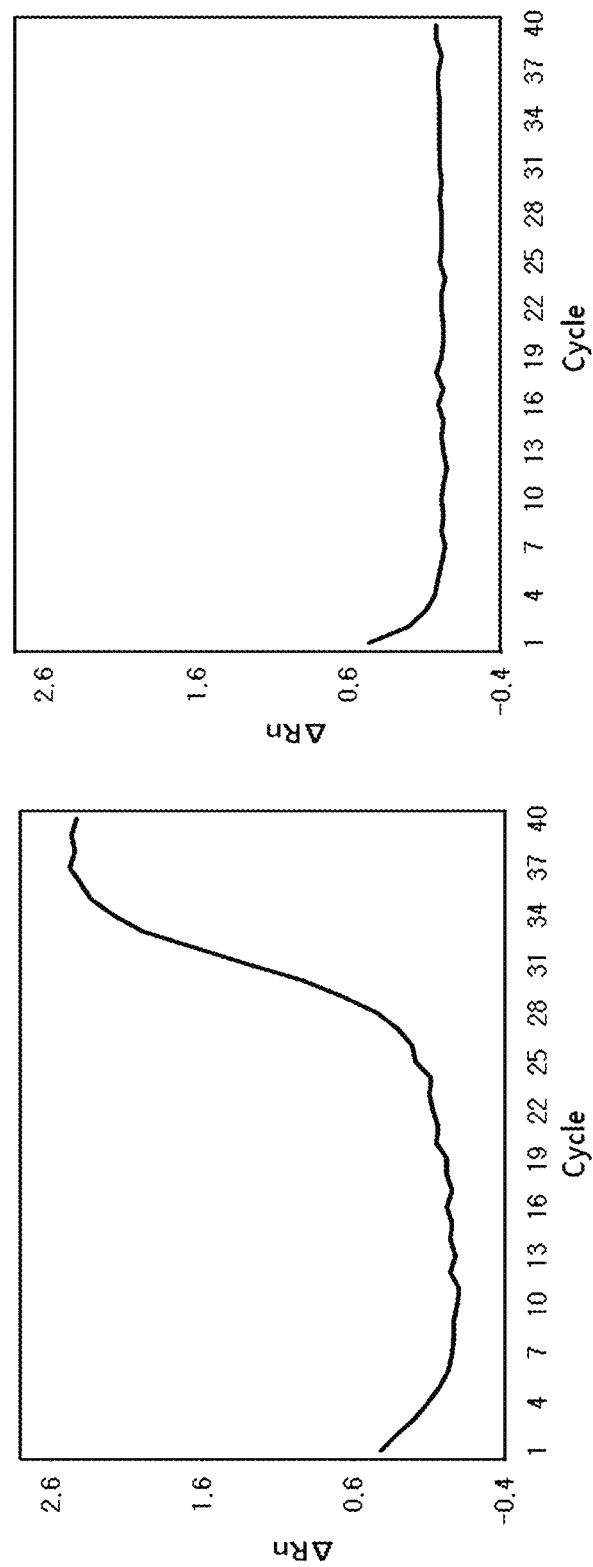
[Fig. 8b]

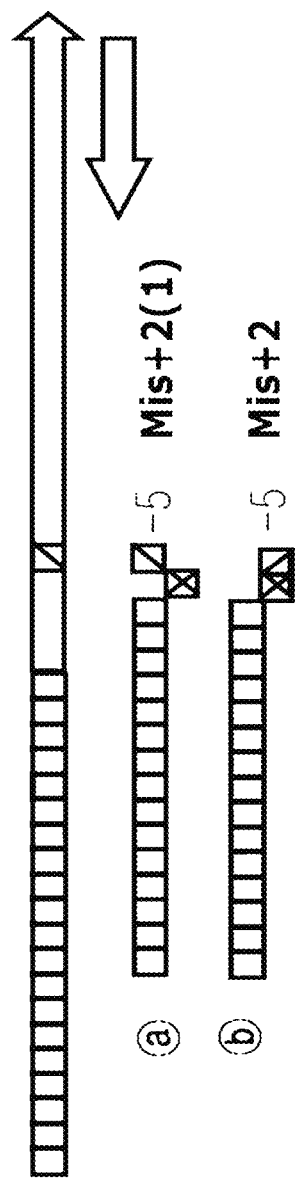
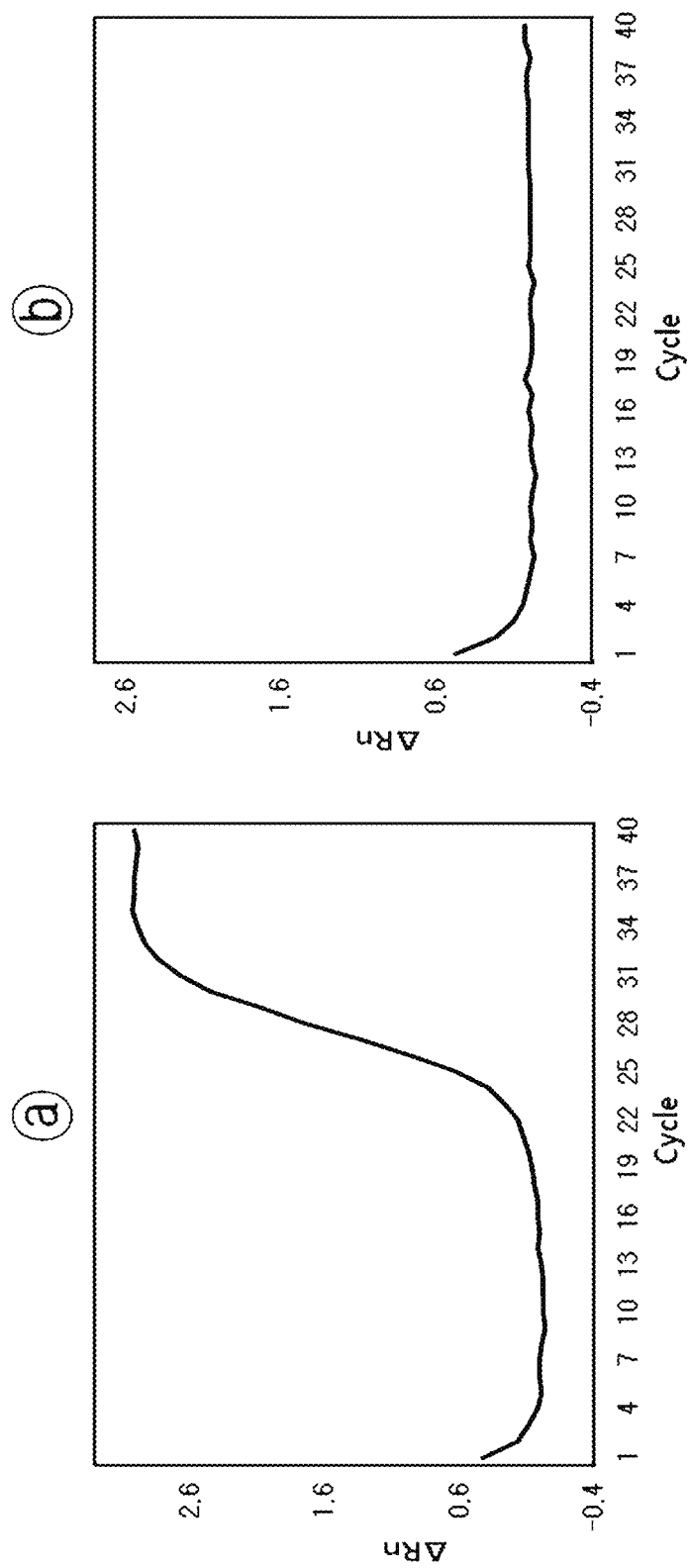

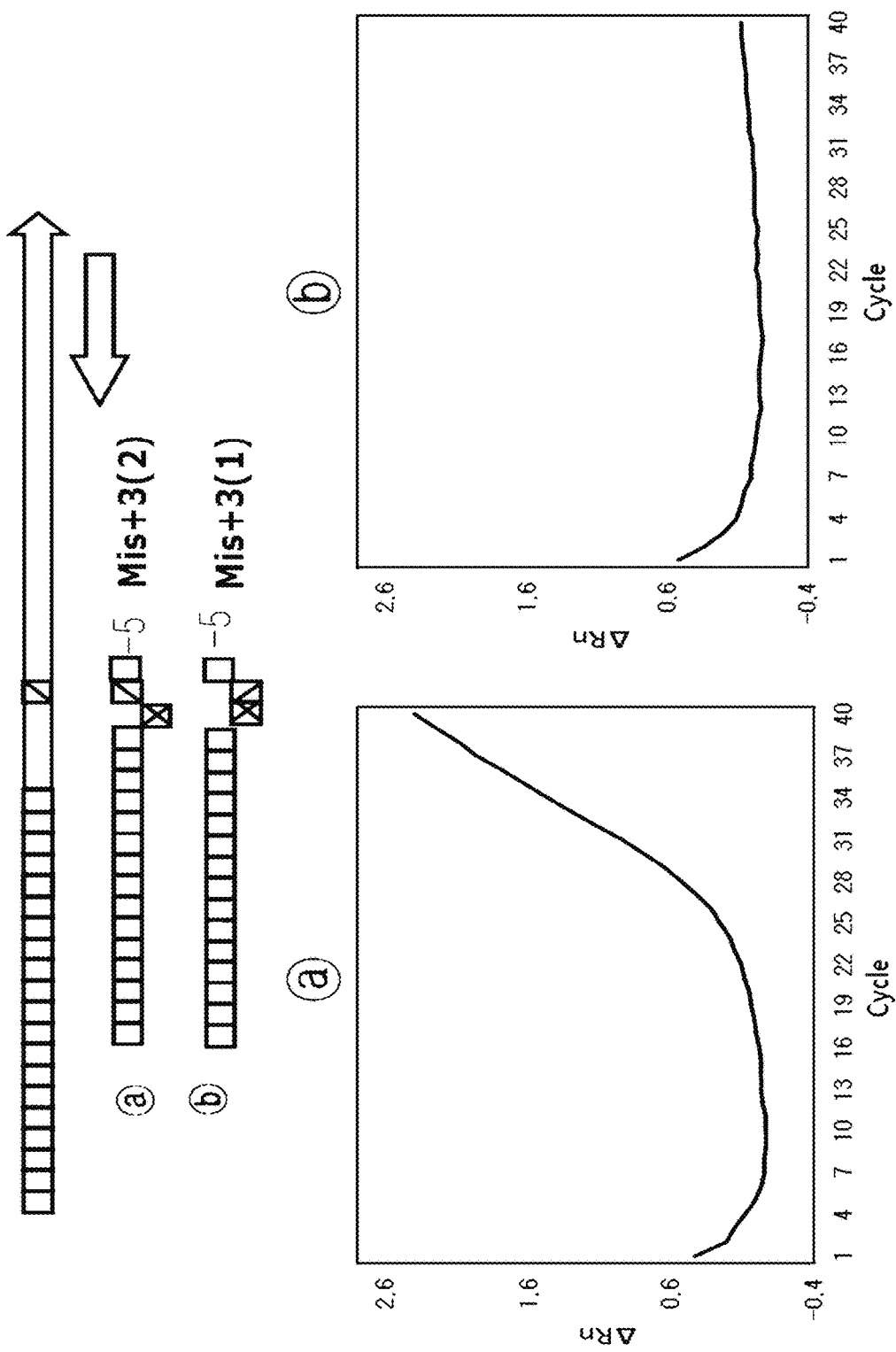

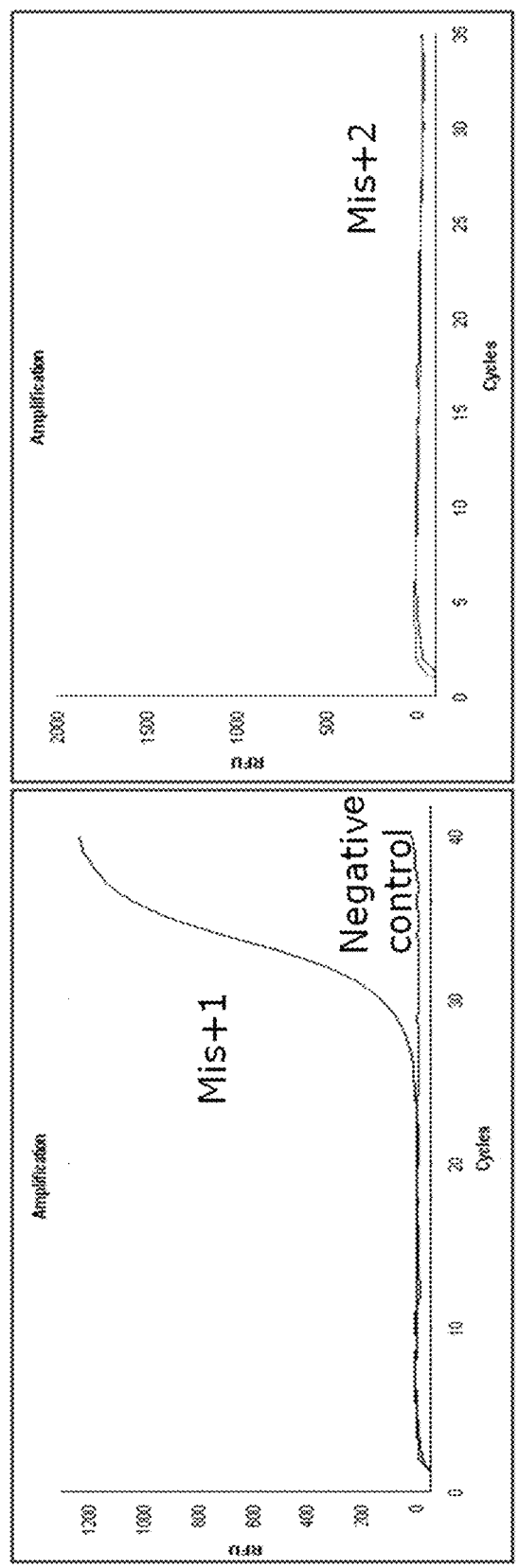
[Fig. 9a]

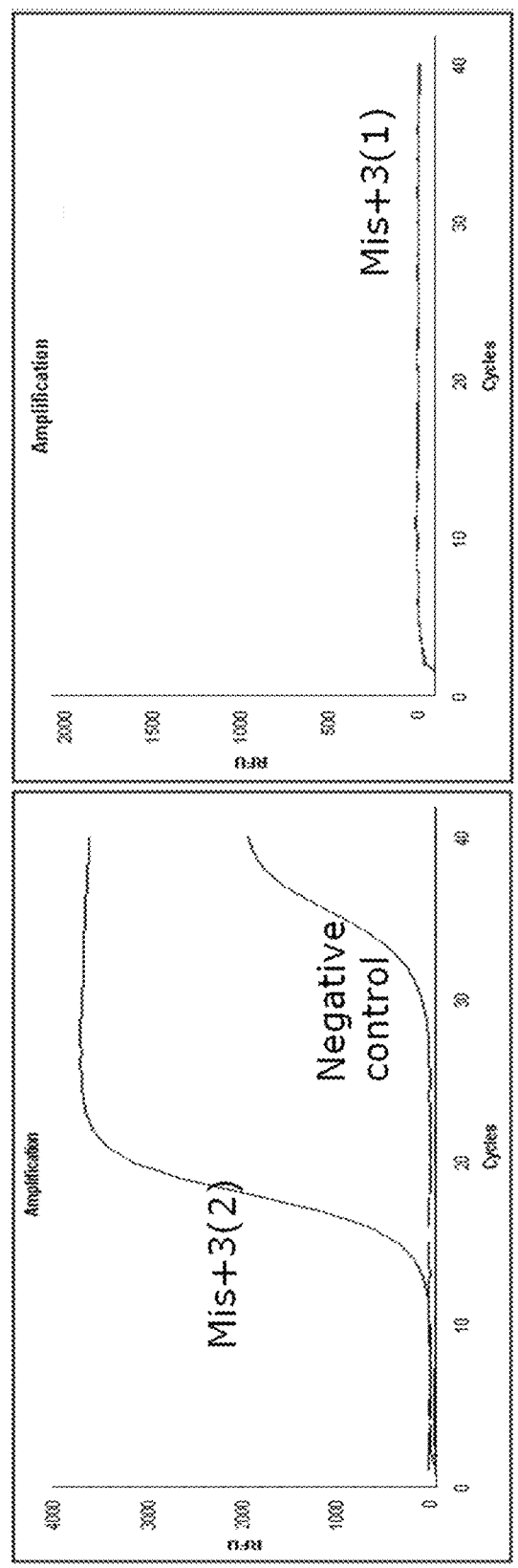
[Fig. 9b]

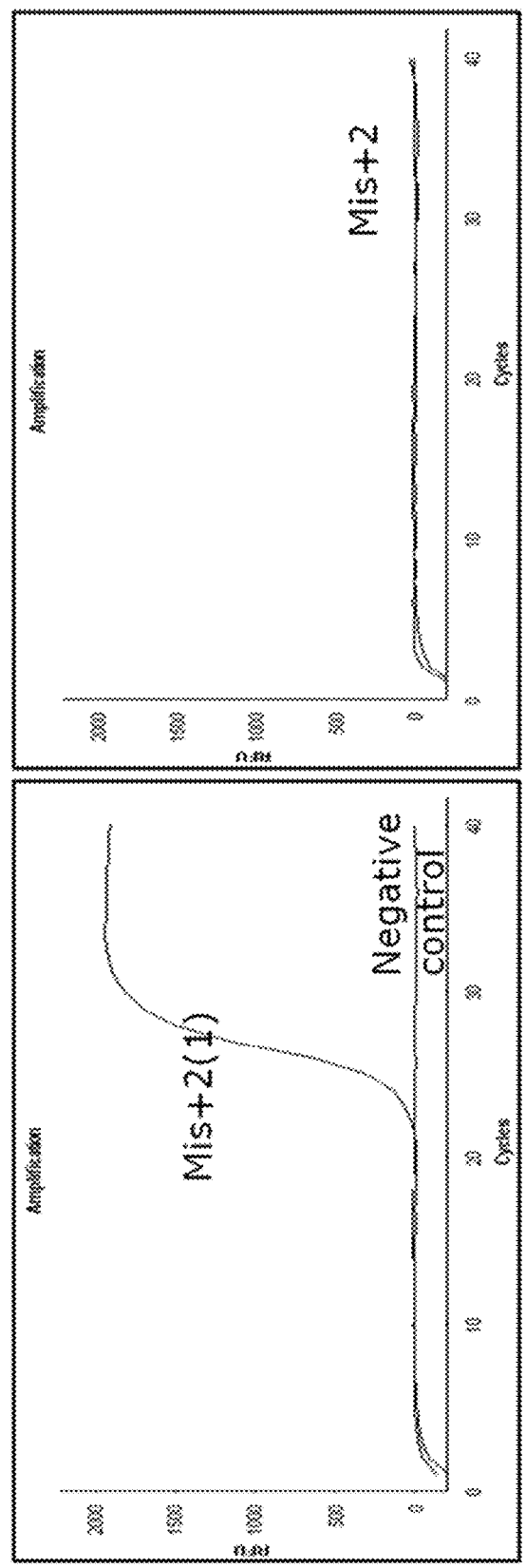
[Fig. 9c]

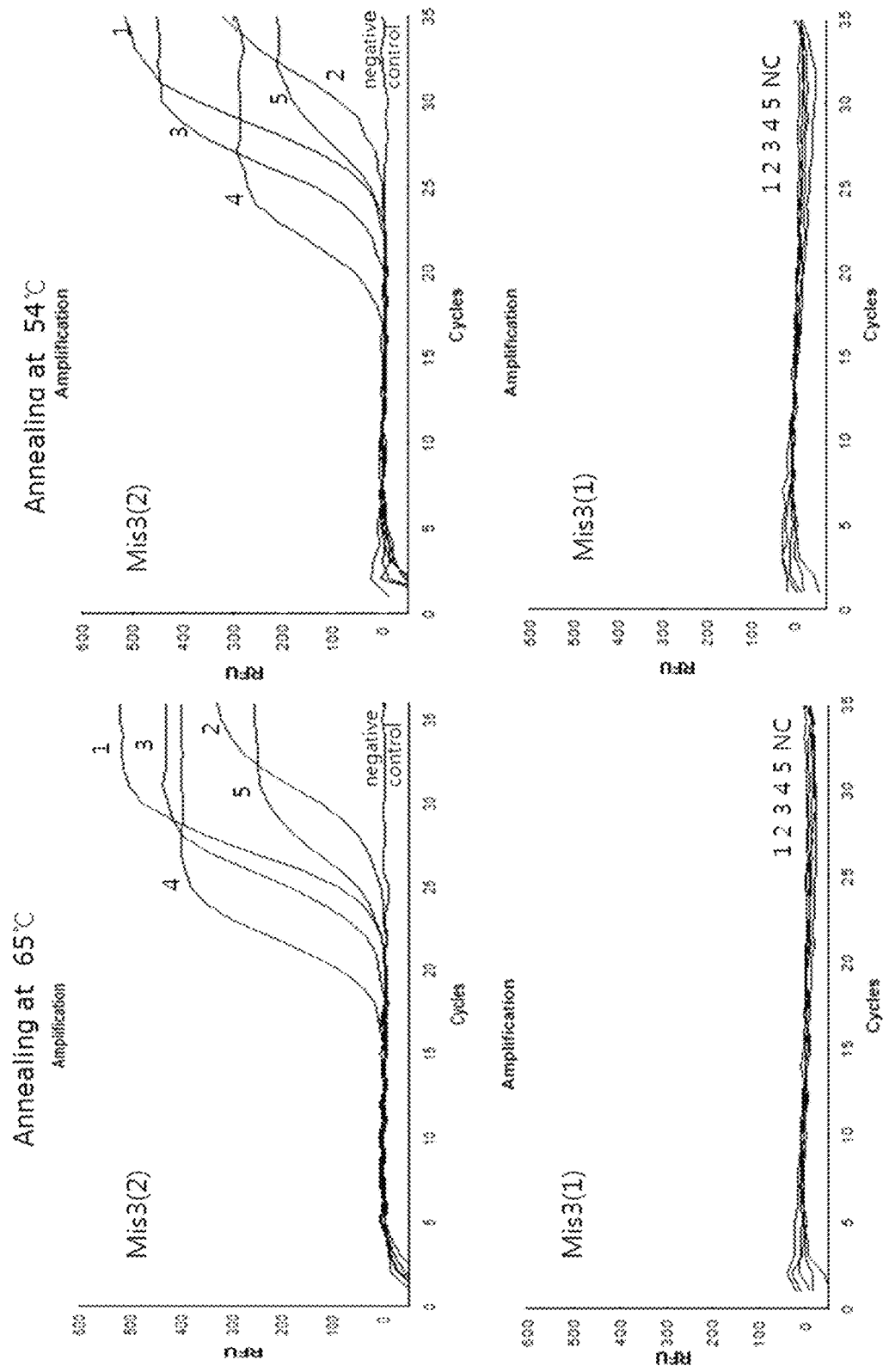
[Fig. 10]

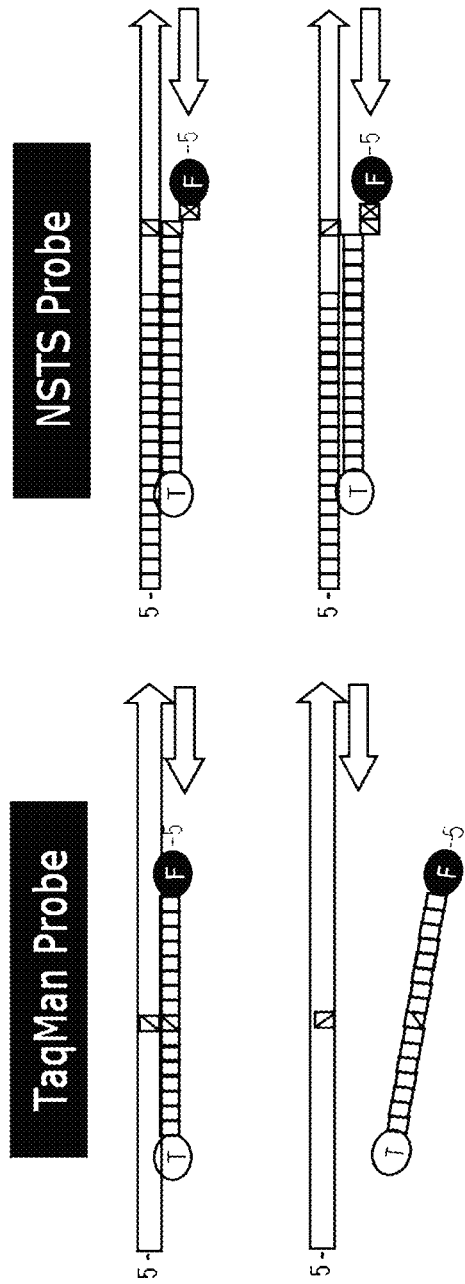
[Fig. 11]

SEQUENCE LISTING

<160> NUMBER OF SEQ ID NOS: 55

<210> SEQ ID NO 1
<211> LENGTH: 22
<212> TYPE: DNA
<213> ORGANISM: Artificial Sequence
<220> FEATURE:
<223> OTHER INFORMATION: primer

<400> SEQUENCE: 1
gccgcgctgg atgaactgat ac          22

<210> SEQ ID NO 2
<211> LENGTH: 22
<212> TYPE: DNA
<213> ORGANISM: Artificial Sequence
<220> FEATURE:
<223> OTHER INFORMATION: probe

<400> SEQUENCE: 2
ccggtatcag ttcatccagc gc          22

<210> SEQ ID NO 3
<211> LENGTH: 21
<212> TYPE: DNA
<213> ORGANISM: Artificial Sequence
<220> FEATURE:
<223> OTHER INFORMATION: primer

<400> SEQUENCE: 3
cggcctgaac agtgagcgaa g          21

<210> SEQ ID NO 4
<211> LENGTH: 23
<212> TYPE: DNA
<213> ORGANISM: Artificial Sequence
<220> FEATURE:
<223> OTHER INFORMATION: probe

<400> SEQUENCE: 4
tccggtatca gttcatccag cgc          23

<210> SEQ ID NO 5
<211> LENGTH: 24
<212> TYPE: DNA
<213> ORGANISM: Artificial Sequence
<220> FEATURE:
<223> OTHER INFORMATION: probe

<400> SEQUENCE: 5
atccggtatc agttcatcca gcgc          24

```
<210> SEQ ID NO 6
<211> LENGTH: 25
<212> TYPE: DNA
<213> ORGANISM: Artificial Sequence
<220> FEATURE:
<223> OTHER INFORMATION: probe

<400> SEQUENCE: 6
catccggtat cagttcatcc agcgc                                         25

<210> SEQ ID NO 7
<211> LENGTH: 24
<212> TYPE: DNA
<213> ORGANISM: Artificial Sequence
<220> FEATURE:
<223> OTHER INFORMATION: primer

<400> SEQUENCE: 7
taccggggtt gctgagtgaa tata                                          24

<210> SEQ ID NO 8
<211> LENGTH: 21
<212> TYPE: DNA
<213> ORGANISM: Artificial Sequence
<220> FEATURE:
<223> OTHER INFORMATION: primer

<400> SEQUENCE: 8
cggcctgaac agtgagcgaa g                                             21

<210> SEQ ID NO 9
<211> LENGTH: 24
<212> TYPE: DNA
<213> ORGANISM: Artificial Sequence
<220> FEATURE:
<223> OTHER INFORMATION: probe

<400> SEQUENCE: 9
cgatatattc actcagcaac cccg                                          24

<210> SEQ ID NO 10
<211> LENGTH: 25
<212> TYPE: DNA
<213> ORGANISM: Artificial Sequence
<220> FEATURE:
<223> OTHER INFORMATION: probe

<400> SEQUENCE: 10
acgatatatt cactcagcaa ccccg                                         25

<210> SEQ ID NO 11
<211> LENGTH: 26
<212> TYPE: DNA
<213> ORGANISM: Artificial Sequence
<220> FEATURE:
<223> OTHER INFORMATION: probe

<400> SEQUENCE: 11
cacgatatat tcactcagca accccg                                        26

<210> SEQ ID NO 12
<211> LENGTH: 20
<212> TYPE: DNA
<213> ORGANISM: Artificial Sequence
<220> FEATURE:
<223> OTHER INFORMATION: probe
```

```
<400> SEQUENCE: 12
ggtatcagtt catccagcgc                                              20

<210> SEQ ID NO 13
<211> LENGTH: 22
<212> TYPE: DNA
<213> ORGANISM: Artificial Sequence
<220> FEATURE:
<223> OTHER INFORMATION: probe

<400> SEQUENCE: 13
atggtatcag ttcatccagc gc                                           22

<210> SEQ ID NO 14
<211> LENGTH: 22
<212> TYPE: DNA
<213> ORGANISM: Artificial Sequence
<220> FEATURE:
<223> OTHER INFORMATION: primer

<400> SEQUENCE: 14
gcagccgcgc tggatgaact ga                                           22

<210> SEQ ID NO 15
<211> LENGTH: 22
<212> TYPE: DNA
<213> ORGANISM: Artificial Sequence
<220> FEATURE:
<223> OTHER INFORMATION: primer

<400> SEQUENCE: 15
aagcagccgc gctggatgaa ct                                           22

<210> SEQ ID NO 16
<211> LENGTH: 22
<212> TYPE: DNA
<213> ORGANISM: Artificial Sequence
<220> FEATURE:
<223> OTHER INFORMATION: primer

<400> SEQUENCE: 16
caaagcagcc gcgctggatg aa                                           22

<210> SEQ ID NO 17
<211> LENGTH: 22
<212> TYPE: DNA
<213> ORGANISM: Artificial Sequence
<220> FEATURE:
<223> OTHER INFORMATION: primer

<400> SEQUENCE: 17
actgataccg gggttgctga gt                                           22

<210> SEQ ID NO 18
<211> LENGTH: 22
<212> TYPE: DNA
<213> ORGANISM: Artificial Sequence
<220> FEATURE:
<223> OTHER INFORMATION: primer

<400> SEQUENCE: 18
gaactgatac cggggttgct ga                                           22

<210> SEQ ID NO 19
<211> LENGTH: 22
```

```
<212> TYPE: DNA
<213> ORGANISM: Artificial Sequence
<220> FEATURE:
<223> OTHER INFORMATION: primer

<400> SEQUENCE: 19
ggatgaactg ataccggggt tg                                           22

<210> SEQ ID NO 20
<211> LENGTH: 23
<212> TYPE: DNA
<213> ORGANISM: Artificial Sequence
<220> FEATURE:
<223> OTHER INFORMATION: probe

<400> SEQUENCE: 20
tccggtatca gttcatccag cgc                                          23

<210> SEQ ID NO 21
<211> LENGTH: 24
<212> TYPE: DNA
<213> ORGANISM: Artificial Sequence
<220> FEATURE:
<223> OTHER INFORMATION: probe

<400> SEQUENCE: 21
ctccggtatc agttcatcca gcgc                                         24

<210> SEQ ID NO 22
<211> LENGTH: 25
<212> TYPE: DNA
<213> ORGANISM: Artificial Sequence
<220> FEATURE:
<223> OTHER INFORMATION: probe

<400> SEQUENCE: 22
actccggtat cagttcatcc agcgc                                        25

<210> SEQ ID NO 23
<211> LENGTH: 25
<212> TYPE: DNA
<213> ORGANISM: Artificial Sequence
<220> FEATURE:
<223> OTHER INFORMATION: probe

<400> SEQUENCE: 23
agaccggtat cagttcatcc agcgc                                        25

<210> SEQ ID NO 24
<211> LENGTH: 23
<212> TYPE: DNA
<213> ORGANISM: Artificial Sequence
<220> FEATURE:
<223> OTHER INFORMATION: primer

<400> SEQUENCE: 24
cgctgtggct gatttcgata acc                                          23

<210> SEQ ID NO 25
<211> LENGTH: 21
<212> TYPE: DNA
<213> ORGANISM: Artificial Sequence
<220> FEATURE:
<223> OTHER INFORMATION: primer

<400> SEQUENCE: 25
```

```
tggctgacgt tcccatgtac c                                              21

<210> SEQ ID NO 26
<211> LENGTH: 21
<212> TYPE: DNA
<213> ORGANISM: Artificial Sequence
<220> FEATURE:
<223> OTHER INFORMATION: probe

<400> SEQUENCE: 26
taggttatcg aaatcagcca c                                              21

<210> SEQ ID NO 27
<211> LENGTH: 21
<212> TYPE: DNA
<213> ORGANISM: Artificial Sequence
<220> FEATURE:
<223> OTHER INFORMATION: probe

<400> SEQUENCE: 27
tcggttatcg aaatcagcca c                                              21

<210> SEQ ID NO 28
<211> LENGTH: 22
<212> TYPE: DNA
<213> ORGANISM: Artificial Sequence
<220> FEATURE:
<223> OTHER INFORMATION: primer

<400> SEQUENCE: 28
tctcggaatg catcgctcag tg                                             22

<210> SEQ ID NO 29
<211> LENGTH: 25
<212> TYPE: DNA
<213> ORGANISM: Artificial Sequence
<220> FEATURE:
<223> OTHER INFORMATION: primer

<400> SEQUENCE: 29
atgctcaatg gatacataga cgagg                                          25

<210> SEQ ID NO 30
<211> LENGTH: 24
<212> TYPE: DNA
<213> ORGANISM: Artificial Sequence
<220> FEATURE:
<223> OTHER INFORMATION: probe

<400> SEQUENCE: 30
agctcaacac tgagcgatgc attc                                           24

<210> SEQ ID NO 31
<211> LENGTH: 24
<212> TYPE: DNA
<213> ORGANISM: Artificial Sequence
<220> FEATURE:
<223> OTHER INFORMATION: probe

<400> SEQUENCE: 31
aactcaacac tgagcgatgc attc                                           24

<210> SEQ ID NO 32
<211> LENGTH: 23
<212> TYPE: DNA
<213> ORGANISM: Artificial Sequence
```

```
<220> FEATURE:
<223> OTHER INFORMATION: primer

<400> SEQUENCE: 32
ctgctgggtg tttatgccta ctt                                               23

<210> SEQ ID NO 33
<211> LENGTH: 22
<212> TYPE: DNA
<213> ORGANISM: Artificial Sequence
<220> FEATURE:
<223> OTHER INFORMATION: primer

<400> SEQUENCE: 33
aagttctcgg catcaccatc cg                                                22

<210> SEQ ID NO 34
<211> LENGTH: 24
<212> TYPE: DNA
<213> ORGANISM: Artificial Sequence
<220> FEATURE:
<223> OTHER INFORMATION: probe

<400> SEQUENCE: 34
cgataaagta ggcataaaca ccca                                              24

<210> SEQ ID NO 35
<211> LENGTH: 24
<212> TYPE: DNA
<213> ORGANISM: Artificial Sequence
<220> FEATURE:
<223> OTHER INFORMATION: probe

<400> SEQUENCE: 35
tgataaagta ggcataaaca ccca                                              24

<210> SEQ ID NO 36
<211> LENGTH: 24
<212> TYPE: DNA
<213> ORGANISM: Artificial Sequence
<220> FEATURE:
<223> OTHER INFORMATION: primer

<400> SEQUENCE: 36
tgatggagca gatgaagatg ctcg                                              24

<210> SEQ ID NO 37
<211> LENGTH: 22
<212> TYPE: DNA
<213> ORGANISM: Artificial Sequence
<220> FEATURE:
<223> OTHER INFORMATION: primer

<400> SEQUENCE: 37
tccagctcac tctcaatggt gg                                                22

<210> SEQ ID NO 38
<211> LENGTH: 23
<212> TYPE: DNA
<213> ORGANISM: Artificial Sequence
<220> FEATURE:
<223> OTHER INFORMATION: probe

<400> SEQUENCE: 38
gtctcgagca tcttcatctg ctc                                               23
```

```
<210> SEQ ID NO 39
<211> LENGTH: 23
<212> TYPE: DNA
<213> ORGANISM: Artificial Sequence
<220> FEATURE:
<223> OTHER INFORMATION: probe

<400> SEQUENCE: 39
ttctcgagca tcttcatctg ctc                                         23

<210> SEQ ID NO 40
<211> LENGTH: 23
<212> TYPE: DNA
<213> ORGANISM: Artificial Sequence
<220> FEATURE:
<223> OTHER INFORMATION: primer

<400> SEQUENCE: 40
cgctgtggct gatttcgata acc                                         23

<210> SEQ ID NO 41
<211> LENGTH: 21
<212> TYPE: DNA
<213> ORGANISM: Artificial Sequence
<220> FEATURE:
<223> OTHER INFORMATION: primer

<400> SEQUENCE: 41
tggctgacgt tcccatgtac c                                           21

<210> SEQ ID NO 42
<211> LENGTH: 24
<212> TYPE: DNA
<213> ORGANISM: Artificial Sequence
<220> FEATURE:
<223> OTHER INFORMATION: probe

<400> SEQUENCE: 42
gatcaggtta tcgaaatcag ccac                                        24

<210> SEQ ID NO 43
<211> LENGTH: 24
<212> TYPE: DNA
<213> ORGANISM: Artificial Sequence
<220> FEATURE:
<223> OTHER INFORMATION: probe

<400> SEQUENCE: 43
aatcaggtta tcgaaatcag ccac                                        24

<210> SEQ ID NO 44
<211> LENGTH: 21
<212> TYPE: DNA
<213> ORGANISM: Artificial Sequence
<220> FEATURE:
<223> OTHER INFORMATION: primer

<400> SEQUENCE: 44
gttcctgacc gtgtggctta c                                           21

<210> SEQ ID NO 45
<211> LENGTH: 23
<212> TYPE: DNA
<213> ORGANISM: Artificial Sequence
<220> FEATURE:
<223> OTHER INFORMATION: primer
```

<400> SEQUENCE: 45
atccccatac gcgcatttcg tag                                        23

<210> SEQ ID NO 46
<211> LENGTH: 23
<212> TYPE: DNA
<213> ORGANISM: Artificial Sequence
<220> FEATURE:
<223> OTHER INFORMATION: probe

<400> SEQUENCE: 46
ggacaggtaa gccacacggt cag                                        23

<210> SEQ ID NO 47
<211> LENGTH: 23
<212> TYPE: DNA
<213> ORGANISM: Artificial Sequence
<220> FEATURE:
<223> OTHER INFORMATION: probe

<400> SEQUENCE: 47
tgacaggtaa gccacacggt cag                                        23

<210> SEQ ID NO 48
<211> LENGTH: 23
<212> TYPE: DNA
<213> ORGANISM: Artificial Sequence
<220> FEATURE:
<223> OTHER INFORMATION: primer

<400> SEQUENCE: 48
ctgctgggtg tttatgccta ctt                                        23

<210> SEQ ID NO 49
<211> LENGTH: 22
<212> TYPE: DNA
<213> ORGANISM: Artificial Sequence
<220> FEATURE:
<223> OTHER INFORMATION: primer

<400> SEQUENCE: 49
aagttctcgg catcaccatc cg                                         22

<210> SEQ ID NO 50
<211> LENGTH: 25
<212> TYPE: DNA
<213> ORGANISM: Artificial Sequence
<220> FEATURE:
<223> OTHER INFORMATION: probe

<400> SEQUENCE: 50
tcgataaagt aggcataaac accca                                      25

<210> SEQ ID NO 51
<211> LENGTH: 24
<212> TYPE: DNA
<213> ORGANISM: Artificial Sequence
<220> FEATURE:
<223> OTHER INFORMATION: probe

<400> SEQUENCE: 51
gcgataaagt aggcataaac accc                                       24

<210> SEQ ID NO 52

```
<211> LENGTH: 22
<212> TYPE: DNA
<213> ORGANISM: Artificial Sequence
<220> FEATURE:
<223> OTHER INFORMATION: primer

<400> SEQUENCE: 52
ccacacggca ttcggcagat at                                              22

<210> SEQ ID NO 53
<211> LENGTH: 24
<212> TYPE: DNA
<213> ORGANISM: Artificial Sequence
<220> FEATURE:
<223> OTHER INFORMATION: primer

<400> SEQUENCE: 53
agcgcctgtt tcttaatcac cata                                            24

<210> SEQ ID NO 54
<211> LENGTH: 25
<212> TYPE: DNA
<213> ORGANISM: Artificial Sequence
<220> FEATURE:
<223> OTHER INFORMATION: probe

<400> SEQUENCE: 54
ggtggaatat ctgccgaatg ccgtg                                           25

<210> SEQ ID NO 55
<211> LENGTH: 24
<212> TYPE: DNA
<213> ORGANISM: Artificial Sequence
<220> FEATURE:
<223> OTHER INFORMATION: probe

<400> SEQUENCE: 55
cgtggaatat ctgccgaatg ccgt                                            24
```

METHOD FOR TESTING A MUTANT GENE THROUGH REAL TIME POLYMERASE CHAIN REACTION USING INHIBITION OF 5'-FLAP ENDONUCLEASE ACTIVITY

TECHNICAL FIELD

The present invention relates to a method for detecting DNA mutations through real time polymerase chain reaction (RT-PCR). More particularly, the present invention relates to a method for inhibiting 5'-flap endonuclease (hereinafter referred to as "PEN"; also referred to as "flap endonuclease") activity of DNA polymerases, specifically family A DNA polymerases, more specifically Taq DNA polymerases, a method for testing for genetic mutations such as single nucleotide polymorphism (hereinafter referred to as SNPs) and the like using the inhibited FEN activity, a method for designing a probe for testing for genetic mutations, and a novel and effective method for effectively and accurately testing for genetic mutations such as a method for applying various types of probes.

BACKGROUND ART

Analysis of genetic mutations is now rapidly growing as its importance in various fields including human genetic disease detection, pharmacogenetics, drug development, microbiology and the like has been emphasized. In the field of genetics, a mutation refers to a change that occurs in a nucleotide sequence constituting DNA, including insertion/deletion of specific genes such as translocation and inversion, and single nucleotide polymorphisms (SNPs). There among, SNPs are the most general type of alteration in a DNA sequence. In the human genome, SNPs occur at a frequency of every 1,000 bases (Sachidanandam, R. et al. 2001. Nature, 409: 928-933). SNPs occur frequently in non-coding regions rather than in coding regions of the human genome (Li, W. H. and Sadler, L. A. 1991. Genetics, 129: 513-523). SNPs in non-coding regions have been employed as a molecular marker in evolutionary studies, while SNPs in coding regions have been employed as a marker in genetic disease studies and detections since SNPs can affect functions of genes, structures or expression of proteins (Kim, S. and Misra, A. 2007. Annu. Rev. Biomed. Eng., 9: 289-320). Further, various methods capable of rapidly and economically analyzing SNPs as molecular markers have been developed with high reliability and sensitivity (Syvanen, A. C. 2001. Nat. Rev. Genet., 2: 930-942; Kirk, B. W. et al. 2002. Nucleic acids Res., 30: 3295-3311; Kwok, P-Y., 2002. Hum. Mutat., 19: 315-323).

SNP analysis using RT-PCR is most extensively employed and its applicability increases with increasing availability of genetic information. As compared to other SNP analysis methods, RT-PCR has advantages in that RT-PCR is fast, has high sensitivity and specificity, is inexpensive and is easily automated. In addition, unlike conventional PCR, RT-PCR does not require electrophoresis using agarose gels and thus has an advantage of minimizing analysis error due to contamination.

In order to analyze SNPs using RT-PCR, probes or primers in the form of oligonucleotides are used and methods using hybridization probes, hydrolysis probes (or TaqMan probes), molecular beacons, scorpion primers, and the like are mainly used. As a mutation analysis method using hybridization probes, a method employing a Light Cycler PCR system from Roche Co. Ltd., using fluorescent resonance energy transfer (FRET) as a principle has been commercially available (Wittwer, C. T. et al., 1997. Bio Techniques, 22: 176-181). Two probes are used in analysis and FRET uses a principle of generating fluorescence when two probes are in close proximity and thus hybridized with a target DNA. Mutation analysis using hybridization probes may be performed by analyzing melting curves after PCR is completed. Namely, in the case where a partial sequence in the target sequence is mismatched with a probe sequence due to mutation, melting temperatures are lower than the case that the target sequence is completely matched with a probe sequence, which leads to differences in melting curves (Lohmann, S., et al., 2000. Biochemica, 4: 23-28). Methods for analyzing mutations using hybridization probes and melting curves are very rapid and the probes used are relatively easy to design. However, melting curves do not always exhibit expected mutation detection ability.

Hydrolysis probe methods use probes to which a reporter and a quencher are attached at both ends together with primers in PCR, and employ a principle of fluorescent resonance energy transfer. Namely, the principle of fluorescent resonance energy transfer refers to a technique that, when the reporter and the quencher are in close proximity, energy transfer from the reporter to the adjacent quencher occurs so as to prevent detection of fluorescence, and as PCR amplification products are increased, probes bound to the target gene are cleaved by 5'→3' nuclease activity of Taq DNA polymerases, thereby causing the reporter to fluoresce. In the hydrolysis probe analysis method (TaqMan probe assay), it is very important to search for appropriate conditions that allow probes to bind to the target base sequence and probes to be degraded by nuclease activity. Namely, PCR conditions (thermal profile) that allow primers and probes used in PCR to hybridize to the target sequence and probes to be cleaved simultaneously are important. In order to satisfy these two requirements, two-step PCR is generally employed. Namely, in two-step PCR, the process of denaturation is performed at 95° C. and then annealing and extension are performed simultaneously at 60° C. which is 7-10° C. lower than Tm. If PCR is performed at extremely high temperature, probes are separated (strand-displace) from the target rather than cleaved by Taq DNA polymerase, and thus fluorescence does not increase (Logan, J. et al. 2009. Caister Academic Press). TaqMan™ probes have an advantage of using various fluorescence materials, which allows SNP detection or mutation analysis. However, this method has to use short probes so as to confer specificity of probes, which necessarily lowers Tm values and makes maintenance of a stable annealing state difficult. In order to overcome this problem, there is a drawback of having to use expensive minor groove binder (MGB) probes or locked nucleic acid (LNA) probes (Letertre, C. et al. 2003. Mol. Cell Probes, 17: 307-311). MGB TaqMan probes are similar to general TaqMan probes, but maintain a stable annealing state under PCR conditions since MGB TaqMan probes have minor grove binders added at 3' end, and accordingly, exhibit a high Tm regardless of their short length (Kutyavin, I. V. et al. 2000. Nucleic Acids Res., 28: 655-661). It is possible to analyze SNPs using amplification refractory mutation system (AMRS) PCR principle with TaqMan probes without using separate modified probes such as MGB probes (Ellison, G. et al. 2010. J. Exp. Clin. Cancer Res., 29:132). However, it is very difficult to identify appropriate PCR conditions capable of distinguishing SNPs through ARMS PCR (Punia P. and S. Aunders. N. http://www.horizonpress.com/pcrbooks).

Molecular beacons and scorpion primers are structured probes including stem-loop structures, show higher specificity than linear probes such as hybridization probes or TaqMan probes, and have excellent ability to recognize mismatches so as to be suitable to discriminate similar sequences or SNPs and alleles. However, considering that it is very difficult to design probes having loop structures, is not easy to obtain desired probes that lead to intended results after general manufacture and examination of various types of probes (Bonnet, G., et al. 1999. Proc. Natl. Acad. Sci. USA, 96: 6171-6176; Broude, N. E. 2002. Trends Biotechnol., 20; 249-256.; Tapp, I. et al. 2000. Biotechniques, 28: 732-738).

The most representative real time PCR is TaqMan analysis, which is a hydrolysis probe analysis method using a 5'→3' exonuclease activity possessed by Taq DNA polymerases as a basic principle. In 1991, Holland et al., disclosed that specific PCR is identified in real time by 5'→3' exonuclease activity of Taq DNA polymerase when probes having a base sequence complementary to a template DNA are used. Furthermore, it was confirmed that the probes used are cleaved by 5'→3' exonuclease activity of Taq DNA without discriminating between probes that are 100% complementary to a template DNA and probes having a non-complementary flap site at the 5'-end (Holland P. M. et al., 1991. Proc. Natl. Acad. Sci., 88: 7276-7280). Thereafter, various RT-PCR techniques were developed using probes modified by fluorescent dyes based on the above method, and are widely used in various applications (Heid, C. A. et al., 1996. Genome Res. 6. 986-994.; Livak K. J. 1999. Genet. Anal., 14:143-149).

In general, DNA polymerases of eukaryotes and archaea include DNA polymerase and DNA endonuclease IV, which is also referred to as FEN1 nuclease (Lieber, M. R., 1997. Bio Essays 19: 233-240), wherein flap endonuclease 1 (FEN1) is known to play an important role in removal of a 5'-flap generated in the course of DNA replication and repair procedures (Rossi, M. L. et al., Chem. Rev. 106, 453-473, Kim, K. et al., 1998. J. Biol. Chem., 273: 8842-8848: Klungland, A. and Lindahl, T. 1997. EMBO J. 16: 3341-3348). Specifically, FEN of eukaryotes is involved in progress of cancers, viral diseases, and the like, which draws growing attention in FEN inhibitors, specifically FEN-1 inhibitors, in order to develop new drugs (Mc Whirter C. et al. 2013. J. Biomol. Screen. 18: 567-75).

Conversely, it is known that, in prokaryotic family A polymerases including DNA polymerases (Taq) derived from *Thermus aquaticus*, 5'-nuclease and DNA polymerase-are located in different domains in a protein and 5'-nuclease has endonuclease (FEN) activity which removes a 5'-flap while also exhibiting general 5'→3' exonuclease activity (Lyamichev, V. et al. 1993. Science, 260:778-783).

From the experimental results by Holland et al., it can be found that FEN activity may be employed instead of 5'→3' exonuclease activity of Taq DNA polymerase when there is a flap site at the 5'-end of the probe used. However, existing methods using TaqMan probes do not discriminate between 5'→3' exonuclease and FEN activity, which are commonly called 5'-nucleases. Invader assay reported in 2005 (Olivier M., 2005. Mutat. Res., 573: 103-110) proposed a method for detecting SNPs using a property of thermostable FEN enzymes, but the method has not been widely used due to low sensitivity resulting from isothermal reactions instead of thermal cycling signal amplification.

DISCLOSURE

Technical Problem

Although various molecular diagnosis techniques as set forth in the above have been developed, there is still a need for molecular diagnosis technology having sufficient sensitivity and specificity. Particularly, although many methods have been used to effectively test for genetic mutations, no test methods satisfy all the concerns required in real clinical trials including test time, cost, specificity, sensitivity and multiplex tests.

Many methods including a TaqMan probe method use complementary binding of allele-specific probes as a basic principle at a specific temperature in order to discriminate SNPs. Since these methods use differences in complementary binding affinity of probes simply depending upon temperature, the methods require additional cost for performing MGB modification, PNA employment and the like so as to maximize the difference in binding affinity. Furthermore, discrimination depending upon temperature does not ensure specificity of all sorts of probes to be discriminated when multiplex SNPs are analyzed simultaneously.

The present invention provides a new test method using RT-PCR based allele-specific probes requiring no further modification, which has advantages in test specificity and multiplex SNP detection using specificity of enzymes instead of discrimination depending upon temperature without incurring further cost.

Technical Solution

The present inventors have found that a new method for effectively detecting single nucleotide polymorphism (SNPs) based on RT-PCR typically used in the art can be established that when 5'-flap endonuclease (FEN) activity of microbial DNA polymerase, representatively Taq DNA polymerase, eliminating a 5'-end non-complementary flap is inhibited by the probe designed through 5'-end site of a probe is located at an SNP site to be detected therefore formed 5'-end non-complementary flap structure according to alleles, and completed the present invention based on this finding.

The present inventors have found a novel method for inhibiting FEN activity of microbial DNA polymerases, representatively Taq DNA polymerases, and by applying such inhibition principle, the present invention provides a method for discriminating between specific binding and non-specific binding of probes to alleles based on properties of Taq DNA polymerases instead of a specific temperature.

The present invention provides a method for designing a probe suitable for FEN specificity of microbial DNA polymerases including Taq DNA polymerases.

Further, the present invention provides a method for testing SNPs at low cost using not only various fluorescent probes such as TaqMan probes, but also non-fluorescent probes such as SYBR Green.

In the present invention, the term "Novel SNP Typing System (NSTS)" refers to a novel system for detecting SNPs according to the present invention using specificity of nuclease activity of DNA polymerase, and is also referred to as "NST probe system". Specifically, the nuclease activity of DNA polymerase may be different according to a 5'-end structure of a probe formed after the probe is hybridized to a target base sequence, and this phenomenon can be employed to construct a novel test system for identifying genetic mutations such as SNPs and the like.

As used herein, the term "TaqMan probe" refers to a modified oligonucleotide in which fluorescent materials (fluorophores) acting as a reporter and a quencher are attached to both ends. Specifically, FAM may be employed as the reporter and TAMRA may be employed as the quencher, without being limited thereto.

As used herein, the term "NSTS/dsp" refers to a case where a double stranded primer is employed in NSTS, and the term "NSTS/TaqMan" refers to a case where TaqMan probe is employed in NSTS. Further, the term "NSTS/sybr-green" refers to a case where SYBR Green is employed in NSTS.

Advantageous Effects

According to the present invention, it is possible to provide an economical means for detecting genetic mutations by applying a new principle that is rapid and has excellent sensitivity and specificity.

According to the present invention, in the case where a probe hybridizes to a target DNA, PCR amplification products are produced when the probe has no base or a base for a 5'-flap structure whereas PCR amplification products are not produced when the probe has 2 or more bases for a 5'-flap structure.

The method for testing a genetic mutation using real time polymerase chain reaction according to the present invention may employ prior primers and probes used in real time PCR such as a double stranded primer having a quencher dye attached at a 5'-end and a reporter dye attached at a 3'-end, or a surface binding agent which is inserted into the double stranded primer or attached to the surface of the double stranded primer, instead of attaching dyes to primers.

Furthermore, the method according to the present invention can effectively employ a TaqMan probe that is the most widely used, when the probe is located at a 5'-end site of a PCR amplification product.

In addition, contrary to prior methods in which difference in annealing temperature of probes is used when multiple DNAs are analyzed simultaneously, the method according to the present invention uses a reaction specificity of enzymes, enabling typing of multiple SNPs without taking annealing temperature into account.

DESCRIPTION OF DRAWINGS

FIGS. 1a and 1b are schematic views depicting a mechanism of an "NST probe system". The system is characterized in that a probe is located at the end site of a PCR product, and a 5'-end of the probe has a 5'-flap structure induced by alleles, by which FEN activity of Taq DNA polymerase is inhibited, enabling SNP typing.

FIG. 2 is a basic schematic view for RT-PCR using a double stranded primer and reaction results thereof.

FIGS. 3a to 3d are schematic views for measuring FEN activity of Taq DNA polymerase using a double stranded primer and results of RT-PCR.

FIGS. 4a and 4b show results for measuring FEN activity for NSTS/dsp probe and NSTS/SYBR-green probe, showing that various types of probes can be exploited in the "NST probe system".

FIGS. 5a and 5b show results for measuring FEN activity for NSTS/TaqMan probe and TaqMan probe, showing that a TaqMan probe can be exploited in the "NST probe system" when the probes are located at the end site of a PCR product.

FIGS. 6a to 6d show experimental results in which inhibition of FEN activity of Taq DNA polymerase is identified by modifying the length of a primer in order to test for a location limit of a probe to which an NSTS/sybr-green system is applied.

FIGS. 7a to 7d show experimental results in which inhibition of FEN activity of Taq DNA polymerase is identified by modifying the length of a primer in order to test for a location limit of a probe to which an NSTS/TaqMan system is applied.

FIGS. 8a to 8d show results of identifying a 5'-end structure of a probe to which an "NST probe system" can be applied.

FIGS. 9a to 9c show results identifying that various probe pairs can be effectively exploited in SNP typing.

FIG. 10 shows RT-PCR results for 5 NSTS/sybr-green probe pairs randomly selected using lambda DNA as a template. The results exhibit an advantage of an "NST probe system" in that multiple probes can be simultaneously employed without taking complementary binding temperature of the probe into account.

FIG. 11 is a schematic view of characteristics of an "NST probe system" as compared with the prior "TaqMan probe system", which exhibits advantages of high specificity and multiplex SNP typing since the "NST probe system" discriminates probes according to a specific 5'-nuclease activity of Taq DNA polymerase rather than differences in temperature.

BEST MODE

The present invention relates to a method for testing for a mutant gene by real time polymerase chain reaction exploiting inhibition of 5'-flap endonuclease activity of DNA polymerases including 5'-flap endonuclease activity.

Further, the present invention relates to a method for testing for a mutant gene exploiting DNA polymerases in which 5'-flap endonuclease activity is inhibited wherein the DNA polymerase is a thermostable DNA polymerase.

Examples of the thermostable DNA polymerase may include wild type thermostable DNA polymerases or variants thereof including *Thermus aquaticus*, *Thermus thermophilus*, *Thermus flavus*, *Bacillus stearothermophilus*, *Thermococcus gorgonarius*, *Thermococcus litoralis*, *Thermococcus kodakaraensis*, *Pyrococcus woesei*, *Pyrococcus furiosus*, *Aeropyrum pernix*, *Aquifex aeolicus*, *Sulfolobus tokodaii*, *Pyrolobus fumarii*, and *Methanopyrus kandleri* derived thermostable DNA polymerases or Ultra DNA polymerases, without being limited thereto. The thermostable DNA polymerases may encompass thermostable DNA polymerases artificially synthesized through genetic engineering.

In the present invention, inhibition of 5'-flap endonuclease activity may be accomplished by placing probes and primers in appropriate locations to inhibit 5'-flap endonuclease activity, by modifying DNA polymerases to inhibit 5'-flap endonuclease activity, by adding 5'-flap endonuclease activity inhibitors, by adjusting other reaction conditions affecting 5'-flap endonuclease activity, for example, by adjusting concentration of salt ions, and the like.

Examples of the present invention demonstrates that the object of the present invention can be accomplished by specifically placing a probe capable of binding to a polymerase chain reaction product a specific location to inhibit 5'-flap endonuclease activity.

Further, the present invention relates to a method for testing for a mutant gene using DNA polymerase, wherein 5'-flap endonuclease activity of DNA polymerase is inhibited by placing a 5'-end of a probe capable of binding to a polymerase chain reaction product within 24-38 bases from the 5'-end of the PCR product.

Furthermore, the present invention relates to a method for testing for a mutant gene using DNA polymerase, wherein the probe for detection has a 5'-end flap site.

Further, the present invention relates to a method for testing for a mutant gene using DNA polymerase, wherein the 5'-end of the probe for detection has a continuous or a non-continuous flap structure of two or more bases.

Further, the mutant gene may have at least one feature selected from single nucleotide polymorphism (SNP), deletion, substitution and insertion at one or more bases.

Furthermore, the present invention relates to a method for testing for a mutant gene by real time polymerase chain reaction exploiting DNA polymerases including 5'-flap endonuclease activity, wherein the mutant gene is tested using a probe capable of inhibiting 5'-flap endonuclease activity of DNA polymerase Further, the present invention relates to a method for testing for a mutant gene using a probe capable of inhibiting 5'-flap endonuclease activity of DNA polymerase, wherein the mutant gene site is located at the 5'-end of the probe capable of binding to a PCR product.

Further, the mutant gene may have at least one feature selected from single nucleotide polymorphism (SNP), deletion, substitution and insertion at one or more bases.

Furthermore, the probe may have a 5'-end flap structure induced depending upon alleles so as to inhibit 5'-flap endonuclease activity of DNA polymerase.

Furthermore, the probe having an induced 5'-end flap structure capable of inhibiting 5'-flap endonuclease activity of DNA polymerase may have a structure in which the 5'-flap has one base, a structure in which the 5'-flap has two bases, or a non-continuous flap structure in which the 5'-flap has two bases and one end base is matched (Mis+3(1)).

Furthermore, a mutant gene having at least one feature selected from deletion, substitution and insertion at one or more bases may be located at the 5'-end of the probe capable of binding to a PCR product.

Further, the present invention relates to a real time polymerase chain reaction kit for testing for a mutant gene, including: a sample DNA, a forward primer, a reverse primer, a probe and a thermostable DNA polymerase, wherein the probe inhibits FEN activity of DNA polymerase.

Further, the present invention relates to a real time polymerase chain reaction kit for testing for a mutant gene, wherein the probe is a dual labeled probe modified simultaneously by a reporter dye and a quencher dye, or an unmodified probe.

Further, the present invention relates to a real time polymerase chain reaction kit for testing for a mutant gene, wherein the forward primer and reverse primer have a complementary binding sequence, respectively, and the probe is a dual labeled probe modified simultaneously by a reporter dye and a quencher dye.

Further, the present invention relates to a real time polymerase chain reaction kit for testing for a mutant gene, wherein a surface binding agent or an intercalating agent, such as SYBR-green, capable of binding to double stranded DNA is added in use of the non-modified probe.

MODE FOR INVENTION

The present invention is aimed at developing a method capable of effectively detecting DNA mutations such as SNPs so as to be clinically employed in genetic disease diagnosis, tumor related gene testing, and the like.

The present invention is characterized in that mutant genes are detected using a pair of primers required for real time PCR, a probe consisting of a base sequence partially complementary to one primer of two primers such as a target gene nucleotide, and a DNA polymerase having 5'-nuclease activity.

The present inventors have found that flap endonuclease (FEN) activity of Taq DNA polymerase recognizing and cleaving a 5'-flap structure may differ depending upon location of the probe that hybridizes upon PCR (FIG. 1a). Based on this finding, a novel method for detecting SNPs using nuclease activity of DNA polymerase (FIG. 1b) can be accomplished.

In the present invention, FEN activity of DNA polymerase recognizing and hydrolyzing a 5'-flap structure may differ depending upon location of a probe to be hybridized upon PCR (FIG. 1). Specifically, FEN activity of DNA polymerase is inhibited when a probe having a 5'-flap structure formed upon hybridization is located at the end site of a PCR amplification product, thereby preventing the probe from being cleaved. More specifically, in the case where the probe hybridizes to a target DNA, PCR amplification products are produced when the 5'-flap of the probe has no base (hereinafter referred to as Mis+0) or the 5'-flap of the probe has a base (hereinafter referred to as Mis+1) whereas the PCR amplification products are not produced when the 5'-flap of the probe has 2 bases (hereinafter referred to as Mis+2) and the 5'-flap of a probe has 3 bases (hereinafter referred to as Mis+3) since FEN activity of DNA polymerase is restricted (FIGS. 3a to 3d).

The primers and probes used in the present invention may include known primers and probes used in real time PCR such as NSTS/dsp employing a DSP (double stranded primer) system using modified oligonucleotides in which a quencher is attached to 5'-end of primers and a fluorophore acting as a reporter is attached to 3'-end of primers (FIG. 4a), NSTS/sybr-green employing unmodified primers and probes applying SYBR green (FIG. 4b), and the like.

Further, in a TaqMan probe system most commonly used in the art, Taq FEN activity of DNA polymerase is not inhibited when the 5'-flap of the probe has 2 or more bases (FIG. 5b). In NSTS/TaqMan in which TaqMan probe is located at the end site of a PCR product, Taq FEN activity of DNA polymerase is inhibited and thus PCR amplification products are not produced when the 5'-flap of the probe has 2 or more bases (FIG. 5a). Accordingly, it can be confirmed that the method according to the present invention can be effectively used when a TaqMan probe is located at end site of the PCR product.

The end site in a PCR product as a precondition for inhibition of FEN activity of DNA polymerase may be restricted within 28 to 34 bases from 5'-flap of the probe to 5'-end site of the PCR product (FIGS. 6a to 6d, FIGS. 7a to 7d), without being limited thereto.

Furthermore, the present invention provides a structure in which NSTS probe pairs that are used in detection of specific SNPs are located at the 5'-end site.

Furthermore, in the present invention, various SNP sites and suitable NSTS probe pairs are verified by NSTS/sybr-green, and thus probes of Mis+1/Mis+2 (FIG. 9a), Mis+3 (2)/Mis+3(1) (FIG. 9b) or Mis+2(1)/Mis+2 (FIG. 9c) pairs are found to be effective in SNP typing. However, use of these probes is not limited to the 5'-end structure.

The present invention provides a novel method for SNP typing capable of overcoming limitations of simultaneous multiplexed analysis and temperature sensitivity of prior methods which use differences in complementary binding temperature in order to identify probes.

In the present invention, RT-PCRs were performed simultaneously using 8 randomly selected probe pairs for NSTS/ sybr-green, from which it was found that those probe pairs could be effectively used in SNP typing simultaneously (FIG. 10). In addition, results of RT-PCRs repeatedly performed at different annealing temperatures (temperature difference, 10° C.) using the identical 8 probe pairs showed the same results (FIG. 10), which indicates that the method of SNP typing according to the present invention is not sensitive to annealing temperature and can discriminate multiple probe pairs using reaction specificity for enzymes, thereby allowing effective multiplex SNP typing (FIG. 11).

Hereinafter, the present invention will be described in more detail with reference to some examples. It should be understood that these examples are provided for illustration only and are not to be construed in any way as limiting the present invention.

Preparation of DNA Sample

Lambda DNA (Catalog # N3011S, New England Bio-Labs) was used as template DNA. 100 pg/μl of lambda DNA was prepared by dilution with distilled water. The prepared DNA was stored in a frozen state before testing.

Preparation of Primers and Probes

Primers were designed so as to amplify a specific fragment of lambda DNA and probes were also designed to have specific sequences capable of hybridizing to amplified products. Probes and primers were modified with fluorescent dyes through application of fluorescence Resonance Energy Transfer (FRET) principle.

RT-PCR Reaction and Confirmation

The prepared lambda DNA, primers and probes were used to perform real time PCR. The used primers and probes are shown in the following examples. A mixture of polymerase and components was 3.1× qPCRMix (31 mM Tris, pH 9.0, 4.65 mM $MgCl_2$, 124 mM KCl, 620 mM methyl glucose, 3.1 mM dNTPs, 3.1 u Taq DNA polymerase, Genotech Corp., Korea). RT-PCR products were confirmed with ABI7500 Real time PCR systems or CFX9600 Real time System.

Example 1: Confirmation of Amplification Curve of RT-PCR Reaction Using Double-Stranded Primer (DSP) System This example is a confirmation test of amplification curve of RT-PCR using DSP/primer forming double strand through hybridization with the position from fourth base of 5'-end of a forward primer. TAMRA as a quencher and FAM as a reporter were linked to the 5'-end of the forward primer and 3'-end of a probe, respectively.

Primers and Probe for Test

Forward primer: 5'-TAMRA-gccgcgctggatgaactgatac-3'

Reverse primer: 5'-cggcctgaacagtgagcgaag-3'

Probe: 5'-ccggtatcagttcatccagcgc-FAM-3'

RT-PCR Conditions:
95° C., 5 min. (1 time)
95° C., 15 sec/60° C., 40 sec/72° C., 30 sec. (35 cycles)
Composition for RT-PCR
To perform RT-PCR, 1 μl (100 pg) of lambda DNA, 1 μl (10 pmol) of each of the above primers and probe, 6.45 ul of 3.1× qPCRMix and distilled water were mixed in a PCR tube to have a final volume of 20 μl.

It was observed that a typical pattern of FAM signals induced from DSP probe by hydrolysis depends on the amount of PCR products during RT-PCR. This result implies that RT-PCR was not inhibited by hybridization of primer/probe forming double strands (FIG. 2).

Example 2: RT-PCR Depending on Structural Features of 5'-End of DSP Probes

In this example, it was confirmed whether change of 5' nuclease activity of DNA polymerase depends on 5'-end structures of DSPs. No flap structure (Mis+0) and flap structures consisting of one base (Mis+1), two bases (Mis+2) or three bases (Mis+3) at 5'-end structure of probes were used in this example.

Primers

Forward primer: 5'-TAMRA-gccgcgctggatgaactgatac-3'

Reverse primer: 5'-cggcctgaacagtgagcgaag-3'

Probes

Mis + 0: 5'-ccggtatcagttcatccagcgc-FAM-3'

Mis + 1: 5'-tccggtatcagttcatccagcgc-FAM-3'

Mis + 2: 5'-atccggtatcagttcatccagcgc-FAM-3'

Mis + 3: 5'-catccggtatcagttcatccagcgc-FAM-3'

RT-PCR Reaction Condition:
95° C., 5 min. (1 time)
95° C., 15 sec—60° C., 30 sec—72° C., 30 sec (40 cycles)
Composition for RT-PCR Reaction
To perform RT-PCR, 1 μl (100 pg) of lambda DNA, 1 μl (10 pmol) of each of the primerset and the probes as above, and 6.45 μl of 3.1× qPCRMix and DW were mixed in a PCR tube to have a final volume of 20 μl.

As seen from FIG. 3, it could be seen that the flap structures of 5'-ends of probes changed 5'-nuclease activity of Taq DNA polymerase. The signaling curves were clearly observed in the case of using Mis+0 probe and Mis+1 probe used the Ct value was greater when the Mis+1 probe was used than when the Mis+0 probe was used. The amplification signal curves were not observed in the case of Mis+2 probe and Mis+3 probe. These results imply that differences of signals reflect differences of DSPs positions at the end of PCR amplified products (TaqMan probe is not) and differences in 5'-end flap structures of probes. In addition, these results imply that the 5'-end flap structure holdbacks 5'→3' exonuclease activity of Taq DNA polymerase to inhibit liberation of FAM from DSP.

Example 3: RT-PCR Using Probes Having 5'-Flap Structures of Various Forms

In this example, in order to confirm inhibition of FEN activity by 5'-end structure in Example 2, change of 5' nuclease activity of Taq DNA polymerase according to the 5'-end structures of DSP, SYBR Green probe and external TaqMan probe were confirmed.

The primers, probes and RT-PCR conditions in this example were as follows.

Primers and Probes for DSP Test (FIG. 4a)

Forward primer: 5'-TAMRA-gccgcgctggatgaactgatac-3'

Reverse primer: 5'-cggcctgaacagtgagcgaag-3'

Probes

```
Mis + 0: 5'-ccggtatcagttcatccagcgc-FAM-3'
Mis + 1: 5'-tccggtatcagttcatccagcgc-FAM-3'
Mis + 2: 5'-atccggtatcagttcatccagcgc-FAM-3'
```

Primers and Probes for SYBR Green Probe Test (FIG. 4b)

```
Forward primer: 5'-gccgcgctggatgaactgatac-3'
Reverse primer: 5'-cggcctgaacagtgagcgaag-3'
```

Probes

```
Mis + 0: 5'-ccggtatcagttcatccagcgc-3'
Mis + 1: 5'-tccggtatcagttcatccagcgc-3'
Mis + 2: 5'-atccggtatcagttcatccagcgc-3'
```

Primers and Probes for External TaqMan Probe Test (FIG. 5a)

```
Forward primer: 5'-taccggggttgctgagtgaatata-3'
Reverse primer: 5'-cggcctgaacagtgagcgaag-3'
```

Probes

```
Mis + 0:
5'-FAM-cgatatattcactcagcaaccccg-TAMRA-3'

Mis + 1:
5'-FAM-acgatatattcactcagcaaccccg-TAMRA-3'

Mis + 2:
5'-FAM-cacgatatattcactcagcaaccccg-TAMRA-3'
```

Primers and Probes for TaqMan Probe Test (FIG. 5b)

```
Forward primer: 5'-gccgcgctggatgaactgatac-3'
Reverse primer: 5'-cggcctgaacagtgagcgaag-3'
```

Probes

```
Mis + 0:
5'-FAM-cgatatattcactcagcaaccccg-TAMRA-3'

Mis + 1:
5'-FAM-acgatatattcactcagcaaccccg-TAMRA-3'

Mis + 2:
5'-FAM-cacgatatattcactcagcaaccccg-TAMRA-3'
```

RT-PCR Reaction Conditions:
95° C., 5 min. (1 time)
95° C., 15 sec—60° C., 30 sec—72° C., 30 sec (35 cycles)
Composition for RT-PCR Reaction To perform RT-PCR, 1 μl (100 pg) of lambda DNA, 1 μl (10 pmol) of each of the primer set and the probes as above, 1 μl of SYBR Green (Takara 10×, in the case of SYBR green test), and 6.45 μl of 3.1× qPCRMix and DW were mixed in a PCR tube to have a final volume of 20 μl.

FIGS. 4 and 5 show that the shapes of PCR amplification signal curves depend on probe type. PCR amplification curves revealed differences according to flap structures of the end of probes in the case of SYBR Green and an external TaqMan probe similar to DSP that hybridizes with forward primers and probes. Mix+0 probe having no flap structure and Mis+1 probe having one base flap structure were hydrolyzed, and Mis+2 probe having two base flap structures did not show any amplification signal curve (FIGS. 4a, 4b and 5a). However, in the case of the TaqMan probe system, the signal was revealed without the probes (FIG. 5b). These results show that there was a difference in signal amplification by 5' nuclease activity of Taq DNA polymerase depending upon the types of 5' end structures. However, in the case of a TaqMan probe located in the middle of PCR products, all probes tested were hydrolyzed regardless of 5'-end structure.

Example 4: Determination of Distance from End of PCR Product to Hybridized Position of Probe Affecting 5'-Endonuclease Activity In this example, it was confirmed whether the distance from an end of PCR products to a hybridized position of probes having 5'-end flap structures located at the end of PCR products has an effect on 5' nuclease activity of Taq DNA polymerase. NSTS/sybr-green probe and NSTS/TaqMan probe were used in this example. Reverse primers and each probe were fixed and forward primers were moved toward the 3'-end of PCR products to change the distance of the primers and the probes. The distance is the number of bases from the 5'-end of the forward primer to the 5'-flap structure of the probe. In the case of NSTS/sybr-green, forward primers corresponding 23 bases, 26 bases, 28 bases, and 30 bases were used (FIG. 6). In the case of NSTS/TaqMan, forward primers corresponding 27 bases, 32 bases, 34 bases, and 38 bases were used (FIG. 7). Mis+2 probe was synthesized by adding arbitrary 2 bases to the 5'-end of the Mis+0 probe sequence.

Primers and Probes for SYBR Green Probe Test

```
Reverse primer: 5'-cggcctgaacagtgagcgaag-3'
```

Probes

```
Mis + 0:
5'-ggtatcagttcatccagcgc-3'

Mis + 2:
5'-atggtatcagttcatccagcgc-3'

① 23 bases forward primer:
5'-gccgcgctggatgaactgatac-3'

② 26 bases forward primer:
5'-gcagccgcgctggatgaactga-3'

③ 28 bases forward primer:
5'-aagcagccgcgctggatgaact-3'

④ 30 bases forward primer:
5'-caaagcagccgcgctggatgaa-3'
```

Primers and Probes for External TaqMan Probe Test

```
reverse primer: 5'-cggcctgaacagtgagcgaag-3'
```

Probes

```
Mis + 0:
5'-FAM-cgatatattcactcagcaaccccg-TAMRA-3'
```

-continued

```
Mis + 2:
5'-FAM-cacgatatattcactcagcaacccg-TAMRA-3'

① 27 bases forward primer:
5'-taccggggttgctgagtgaatata-3'

② 32 bases forward primer:
5'-actgataccggggttgctgagt-3'

③ 34 bases forward primer:
5'-gaactgataccggggttgctga-3'

④ 38 bases forward primer:
5'-ggatgaactgataccggggttg-3'
```

RT-PCR Reaction Condition:
95° C., 5 min (1 time)
95° C., 15 sec—60° C., 30 sec—72° C., 30 sec (35 cycles)
Composition for RT-PCR Reaction To perform RT-PCR, 1 μl (100 pg) of lambda DNA, 1 μl (10 pmol) of each of the primer set and the probes as above, 1 μl of SYBR Green (Takara 10×, in the case of SYBR green test), and 6.45 μl of 3.1× qPCRMix and DW were mixed in a PCR tube to have a final volume of 20 μl.

PCR amplification curves appeared using forward primers having distances of more than 30 bases from the 5' end of the hybridized probe in the case of NSTS/sybr-green test and 34 bases in the case of NSTS/TaqMan test (FIGS. 6 and 7). The results imply that FEN nuclease of Taq DNA polymerase requires adequate length of bases (about 28-34 bases) to cleave 5' flap structure and FEN nuclease will not act on probes having over the adequate distance. Therefore, in order to discriminate target mutation (SNP) from normal DNA using NSTS, it is important to maintain the distance (not more than about 28-30 bases) in design of primers/probes for diagnosis.

Example 5: Probe Pairs Test for SNP Typing

This example shows that 5' end structures of NSTS probes have an effect on FEN activity of DNA polymerase for application of SNP typing. NSTS/DSP probe pairs were designed depending upon arbitrary mutation bases (SNP point) and used for testing.

The probe (Mis+0) having no flap structure at the 5'-end and the probe (Mis+1) having one base flap structure, ② the probe (Mis+1) having one base flap structure at 5'-end and the probe (Mis+2) having two base flap structure, ③ the probe (Mis+2(1)) having one base flap structure of second base at 5'-end and the probe (Mis+2) having two bases flap structure. ④ the probe (Mis+3(2)) having one base flap structure of third base at 5'-end and the probe (Mis+3 (1)) having two bases flap structure of second and third bases at 5'-end (FIG. 8).

Primes and Probes for Test

```
Forward primer: 5'-TAMRA-gccgcgctggatgaactgatac-3'
Reverse primer: 5'-cggcctgaacagtgagcgaag-3'
```

① Probe set

```
ⓐ Mis + 0: 5'-ccggtatcagttcatccagcgc-FAM-3'
ⓑ Mis + 1: 5'-tccggtatcagttcatccagcgc-FAM-3'
```

② Probe Set

```
ⓐ Mis + 1: 5'-tccggtatcagttcatccagcgc-FAM-3'
ⓑ Mis + 2: 5'-atccggtatcagttcatccagcgc-FAM-3'
```

③ Probe Set

```
ⓐ Mis + 2(1): 5'-ctccggtatcagttcatccagcgc-FAM-3'
ⓑ Mis + 2: 5'-atccggtatcagttcatccagcgc-FAM-3'
```

④ Probe Set

```
ⓐ Mis + 3(2): 5'-actccggtatcagttcatccagcgc-FAM-3'
ⓑ Mis + 3(1): 5'-agaccggtatcagttcatccagcgc-FAM-3'
```

RT-PCR Reaction Condition:
95° C., 5 min (1 time)
95° C., 15 sec—60° C., 30 sec—72° C., 30 sec (40 cycles)
Composition for RT-PCR Reaction To perform RT-PCR, 1 μl (100 pg) of lambda DNA, 1 μl (10 pmol) of above primers and a probe among of above probes, 6.45 μl of 3.1× qPCRMix and DW were mixed in a PCR tube to have a final volume of 20 μl.

For SNP typing using FEN activity of Taq DNA polymerase controlled by the flap structures, four probe pairs were designed according to the proposed flap structures. In this example, the test using the ⓑ probe provided a lower Ct value and a lower PCR amplification curve than the test using the ⓐ probe. Especially, the tests using the probe sets ②, ③, ④ showed that PCR amplification curves were on/off controlled, and provided a merit of detection of alleles for SNP typing using these kinds of probe sets.

Example 6: Verification of Application Using Various NSTS/Sybr-Green Probe Pairs To confirm practical use of SYBR Green dye for SNP typing, various 5'-end structures of NSTS/sybr-green probes were tested in this example. SNP point was arbitrarily set in lambda DNA and DSP probe pairs were selected in consideration of 5'-end structures. Mis+1 and Mis+2 (FIG. 9a), Mis+3(2) and Mis+3(1) (FIG. 9b), and Mis+2(1) and Mis+2 are used as DSP pairs in this example.

Primers and Probes for the Test (FIG. 9a)

```
Forward primer: 5'-cgctgtggctgatttcgataacc-3'
Reverse primer: 5'-tggctgacgttcccatgtacc-3'
```

Probes

```
Mis + 1: 5'-taggttatcgaaatcagccac-3'
Mis + 2: 5'-tcggttatcgaaatcagccac-3'
```

Primers and Probes for the Test (FIG. 9b)

```
Forward primer: 5'-tctcggaatgcatcgctcagtg-3'
Reverse primer: 5'-atgctcaatggatacatagacgagg-3'
```

Probes

```
Mis + 3(2): 5'-agctcaacactgagcgatgcattc-3'
Mis + 3(1): 5'-aactcaacactgagcgatgcattc-3'
```

Primers and Probes for the Test (FIG. 9c)

```
Forward primer: 5'-ctgctgggtgtttatgcctactt-3'
Reverse primer: 5'-aagttctcggcatcaccatccg-3'
```

Probes

```
Mis + 2(1): 5'-cgataaagtaggcataaacaccca-3'
Mis + 2: 5'-tgataaagtaggcataaacaccca-3'
```

RT-PCR Reaction Conditions:
95° C., 5 min (1 time)
95° C., 15 sec—60° C., 30 sec—72° C., 30 sec (40 cycles)
Composition for RT-PCR Reaction To perform RT-PCR, 1 μl (100 pg) of lambda DNA, 1 μl (10 pmol) of each of the primer set and the probes as above, 1 μl of SYBR Green (10×, Takara), 6.45 μl of 3.1× qPCRMix and DW were mixed in a PCR tube to have a final volume of 20 μl.

It was confirmed that alleles were discriminated by PCR amplification curves depending on formation of flap structures according to matching or non-matching 5'-ends of probes with SNP point using SYBR-Green. It is possible to clearly discriminate SNP typing due to non-generation of the PCR amplification curves in the case of non-matching with the SNP point, or vice versa in the case of matching. Therefore, the present invention provides an economical and simple diagnostic method using inexpensive intercalating agents or surface binding agents, like SYBR Green, instead of expensive fluorescent dyes.

Example 7: Verification of Broad Annealing Temperature on Action of NSTS Probes in RT-PCR This example was performed to confirm an effect of the annealing temperature in RT-PCR on NSTS probes discriminated by enzymatic specificity. This example was performed under the same conditions using NSTS/sybr-green probes excluding the annealing temperatures. Mis+3(2) probe having one base flap structure of the third base at the 5'-end and the Mis+3(1) probe having two base flap structure of the first and third bases at the 5'-end are used as follows.

Primers and Probes for DSP Probe Test

```
Forward primer 1a: 5-TGATGGAGCAGATGAAGATGCTCG-3
Reverse primer 1as: 5-TCCAGCTCACTCTCAATGGTGG-3
```

Probes

```
Mis + 3(2)/1: 5-GTCTCGAGCATCTTCATCTGCTC-3
Mis + 3(1)/1: 5-TTCTCGAGCATCTTCATCTGCTC-3
Forward primer 2a: 5-CGCTGTGGCTGATTTCGATAACC-3
Reverse primer 2as: 5-TGGCTGACGTTCCCATGTACC-3
```

Probes

```
Mis + 3(2)/2: 5-GATCAGGTTATCGAAATCAGCCAC-3
Mis + 3(1)/2: 5-AATCAGGTTATCGAAATCAGCCAC-3
Forward primer 3a: 5-GTTCCTGACCGTGTGGCTTAC-3
Reverse primer 3as: 5-ATCCCCATACGCGCATTTCGTAG-3
```

Probes

```
Mis + 3(2)/3: 5-GGACAGGTAAGCCACACGGTCAG-3
Mis + 3(1)/3: 5-TGACAGGTAAGCCACACGGTCAG-3
Forward primer 4a: 5-CTGCTGGGTGTTTATGCCTACTT-3
Reverse primer 4as: 5-AAGTTCTCGGCATCACCATCCG-3
```

Probes

```
Mis + 3(2)/4: 5-TCGATAAAGTAGGCATAAACACCCA-3
Mis + 3(1)/4: 5-GCGATAAAGTAGGCATAAACACCC-3
Forward primer 5a: 5-CCACACGGCATTCGGCAGATAT-3
Reverse primer 5as: 5-AGCGCCTGTTTCTTAATCACCATA-3
```

Probes

```
Mis + 3(2)/5: 5-GGTGGAATATCTGCCGAATGCCGTG-3
Mis + 3(1)/5: 5-CGTGGAATATCTGCCGAATGCCGT-3
```

RT-PCR Reaction Conditions 1:
95° C., 5 min (1 time)
95° C., 15 sec—65° C., 30 sec—72° C., 30 sec (40 cycles)
RT-PCR Reaction Conditions 2:
95° C., 5 min (1 time)
95° C., 15 sec—54° C., 30 sec—72° C., 30 sec (40 cycles)
Composition for RT-PCR Reaction To perform RT-PCR, 1 μl (100 pg) of lambda DNA, 1 μl (5 pmol) of each of the primer set and the probes as above, 1 μl of SYBR Green (10×, Takara), 4 μl of 5× qPCRMix (50 mM Tris, pH 9.0, 7.5 mM MgCl$_2$, 300 mM KCl, 1 M methyl glucose, 500 mM (NH$_4$)$_2$SO$_4$, 5 mM dNTPs, 5 μl Taq DNA polymerase, Genotech Corp. Korea) and DW were mixed in a PCR tube to have a final volume of 20 μl.

It could be seen that Ct values and patterns of amplification curves were similar at different annealing temperatures with a temperature difference of 10° C. or higher in PCR and the signals were clearly discriminated according to specificity of probes (FIG. 10). The discrimination method using specificity of enzymatic reaction caused by allele specific probes was not affected by the annealing temperature. This result shows that the present invention is very effective for simultaneous analysis of SNPs.

INDUSTRIAL APPLICABILITY

The present invention relates to a novel genetic mutation detection system adopting a novel principle having simple, fast and economical features. Therefore, the present invention provides a molecular diagnostics method for medicine, pharmacy, agriculture, livestock, marine, etc.

PRETEXT FOR SEQUENCE LISTS

The lists of sequences are arbitrarily designed and synthesized for primers and probes to illustrate the methods of genetic mutation detection.

This invention was supported by the Technological Innovation R&D Program (S2166257) funded by the Small and Medium Business Administration (SMBA, Korea).

The invention claimed is:

1. A method of determining a mutation of a gene, the method comprising:
   providing a template DNA for testing, the template DNA comprising a DNA strand that contains a pre-identified potential SNP location in its sequence;
   performing a real-time PCR of the template DNA in the presence of a first primer, a second primer, a DNA polymerase, and a probe to provide a PCR product strand which comprises a primer portion originating from the first primer and a polymerized portion extending from the primer portion, in which the polymerized portion comprises a base at a location corresponding to the pre-identified potential SNP location of the DNA strand,
   wherein the probe is configured to enable fluorescence resonance energy transfer (FRET),
   wherein the probe comprises a first portion and a second portion that extends from the first portion to a 5'-end of the probe,
   wherein the first portion of the probe is designed to be complementary to at least part of the first primer such that the probe hybridizes to the PCR product strand during the real-time PCR,
   wherein the second portion of the probe is designed to comprise a first base at the 5'-end of the probe and a second base next to the first base such that the second base corresponds to the base of the PCR product strand at the location corresponding to the pre-identified potential SNP location of the DNA strand and further such that the first base is not complementary to its corresponding base of the PCR product strand,
   wherein, when the probe hybridizes to the PCR product strand during the real-time PCR, the first base and the second base of the second portion provide a flap with one base at the 5'-end of the probe if the template DNA does not have a mutation at the pre-identified potential SNP location,
   wherein, when the probe hybridizes to the PCR product strand during the real-time PCR, the first base and the second base of the second portion provide a flap with two or more bases at the 5'-end of the probe if the template DNA has a mutation at the pre-identified potential SNP location,
   wherein the DNA polymerase has a 5'-flap endonuclease (FEN) activity for a flap with one base while the 5'-flap endonuclease (FEN) activity is inhibited for a flap with two or more bases,
   wherein when the probe has a flap with one base, the DNA polymerase hydrolyzes the flap with one base and performs DNA polymerization during the real-time PCR, which will generate a FRET signal, wherein when the probe has a flap with two or more bases, the 5'-flap endonuclease (FEN) activity of the DNA polymerase is inhibited and does not perform DNA polymerization during the real-time PCR, which does not generate a FRET signal, determining that the template DNA does not have a mutation at the pre-identified potential SNP location if a FRET signal is detected; and determining that the template DNA does have a mutation at the pre-identified potential SNP location if a FRET signal is not detected.

2. The method of claim 1, wherein the DNA polymerase is a thermostable DNA polymerase.

3. The method of claim 1, wherein the probe comprises a reporter dye and a quencher dye.

4. The method of claim 1, wherein the probe is a dual labeled probe modified by both a reporter dye and a quencher dye.

5. The method of claim 1, wherein a 3'-end of the probe is modified by a reporter dye and the 5'-end of the probe is modified by a quencher dye.

6. The method of claim 1, wherein the probe is an unmodified probe.

7. The method of claim 6, wherein an intercalating agent capable of binding to surfaces of DNA double bonds is added in use of the unmodified probe.

8. The method of claim 6, wherein a surface binding agent capable of binding to the surfaces of the DNA double bonds is added in use of the unmodified probe.

* * * * *